US011781950B2

(12) United States Patent
Whitkanack et al.

(10) Patent No.: US 11,781,950 B2
(45) Date of Patent: Oct. 10, 2023

(54) INTEGRATED DISSOLUTION PROCESSING AND SAMPLE TRANSFER SYSTEM

(71) Applicant: SOTAX Corporation, Westborough, MA (US)

(72) Inventors: Kevin Whitkanack, Stow, MA (US); Philip Gauthier, Worcester, MA (US); Robert Houser, North Attleboro, MA (US); Tye Fowler, Uxbridge, MA (US); Ryan Kelly, Shirley, MA (US)

(73) Assignee: SOTAX Corporation, Westborough, MA (US)

( * ) Notice: Subject to any disclaimer, the term of this patent is extended or adjusted under 35 U.S.C. 154(b) by 0 days.

(21) Appl. No.: 16/984,011

(22) Filed: Aug. 3, 2020

(65) Prior Publication Data

US 2021/0108992 A1  Apr. 15, 2021

Related U.S. Application Data

(63) Continuation of application No. 16/600,891, filed on Oct. 14, 2019, now Pat. No. 10,732,080.

(51) Int. Cl.
*G01N 1/10* (2006.01)
*G01N 1/40* (2006.01)
(Continued)

(52) U.S. Cl.
CPC ............. *G01N 1/10* (2013.01); *G01N 1/4055* (2013.01); *G01N 2001/4061* (2013.01)

(58) Field of Classification Search
None
See application file for complete search history.

(56) References Cited

U.S. PATENT DOCUMENTS 3,791,222 A * 2/1974 Goodhart ................ B01F 35/20
73/866
4,226,114 A   10/1980 Hagedorn
(Continued)

FOREIGN PATENT DOCUMENTS

| CN | 105784953 A | 7/2016 |
| CN | 206096096 U | 4/2017 |
| WO | 2010099519 A1 | 9/2010 |

OTHER PUBLICATIONS

International Search Report and Written Opinion, PCT/US2020/055485, dated Mar. 24, 2021, 22 pages.

(Continued)

*Primary Examiner* — Neil N Turk
(74) *Attorney, Agent, or Firm* — Potomac Law Group, PLLC; Reza Mollaaghababa; Reza Sadr

(57) ABSTRACT

In one aspect, a system for controlled temporal extraction of ingredients of a pharmaceutical dosage form is disclosed, which comprises at least one reservoir for storing a fluid comprising a solvent, a cell having at least one inlet port in fluid communication with said reservoir for receiving a flow of the fluid from the reservoir and an outlet port through which fluid can exit the cell, where the cell is configured to receive a pharmaceutical dosage form. The system can further include an in-line heater disposed in proximity of the inlet port of the cell for heating the fluid to an elevated temperature prior to entry thereof into the cell, and a pump for causing fluid circulation between said reservoir and said cell.

15 Claims, 21 Drawing Sheets

(51) Int. Cl.
*G01N 33/15* (2006.01)
*A61K 9/16* (2006.01)
*A61K 9/20* (2006.01)

(56) References Cited

U.S. PATENT DOCUMENTS

| | | | |
|---|---|---|---|
| 4,335,438 A * | 6/1982 | Smolen | G01N 13/00 |
| | | | 73/866 |
| 4,335,738 A | 6/1982 | Nassir | |
| 4,578,244 A * | 3/1986 | Cosgrove, Jr. | G01N 13/00 |
| | | | 422/65 |
| 4,879,917 A * | 11/1989 | Eppelmann | G01N 13/00 |
| | | | 73/866 |
| 5,589,649 A | 12/1996 | Brinker | |
| 5,816,701 A | 10/1998 | Martin | |
| 5,827,984 A * | 10/1998 | Sinnreich | B01F 21/10 |
| | | | 73/866 |
| 6,727,480 B2 * | 4/2004 | Fernando | B01F 21/00 |
| | | | 73/866 |
| 7,021,163 B2 * | 4/2006 | Kyne | G01N 33/15 |
| | | | 73/866 |
| 7,585,465 B2 | 9/2009 | Lee | |
| 10,732,080 B1 | 8/2020 | Whitkanack et al. | |
| 2001/0043954 A1 | 11/2001 | Sweet | |
| 2001/0050881 A1 | 12/2001 | Depaoli | |
| 2004/0168529 A1 * | 9/2004 | Carlson | C40B 40/04 |
| | | | 436/178 |
| 2005/0003550 A1 | 1/2005 | Kyne | |
| 2008/0311267 A1 * | 12/2008 | Leigh | A61P 3/02 |
| | | | 426/520 |
| 2010/0107752 A1 * | 5/2010 | Fernando | G01F 23/20 |
| | | | 73/866 |
| 2016/0327466 A1 * | 11/2016 | Kalbermatten | B01F 33/813 |
| 2019/0046973 A1 | 2/2019 | Muller | |

OTHER PUBLICATIONS

International Invitation to Pay Additional fees and Partial Search Report, PCT/US2020/055485, dated Feb. 3, 2021, 18 pages.
Kakhi et al., "Mathematical modeling of the fluid dynamics in the flow-through cell", International Journal of Pharmaceutics, Elsevier, NL, vol. 376, No. 1-2, Jul. 6, 2009, pp. 22-40.

* cited by examiner

INTEGRATED DISSOLUTION PROCESSING AND SAMPLE TRANSFER SYSTEM

CROSS REFERENCE TO RELATED APPLICATIONS

This Application claims priority to and is a continuation of U.S. patent application Ser. No. 16/600,891, filed on Oct. 14, 2019, the teachings of which are incorporated herein by reference in their entirety.

BACKGROUND

The present invention relates generally to methods and systems for rapid and controlled extraction of ingredient(s) of a pharmaceutical dosage form, e.g., a tablet.

Each year, millions of pharmaceutical dosages are manufactured and consumed. Assay, content uniformity and dissolution testing of all solid oral pharmaceutical dosage forms is required. Such testing is used as a means of quality control as well as a means for correlating in-vitro and in-vivo drug release characteristics.

Although conventional systems for testing are known, such systems exhibit certain shortcomings. For example, such systems may not provide the requisite analysis speed in order to provide critical quality feedback used to control a manufacturing process.

Accordingly, there is a need for accelerated methods and systems for controlled temporal extraction of ingredients of pharmaceutical dosage forms.

SUMMARY

In one aspect, a system for controlled temporal extraction of ingredients of a pharmaceutical dosage form is disclosed, which comprises at least one reservoir for storing a fluid comprising a solvent, a cell having at least one inlet port in fluid communication with said reservoir for receiving a flow of the fluid from the reservoir and an outlet port through which fluid can exit the cell, where the cell is configured to receive a pharmaceutical dosage form. The system can further include an in-line heater disposed in proximity of the inlet port of the cell for heating the fluid to an elevated temperature prior to entry thereof into the cell, and a pump for causing fluid circulation between the reservoir and the cell. The fluid flow over the pharmaceutical dosage form within the cell causes extraction of at least one ingredient of the dosage form into the flowing fluid such that the fluid exiting the cell contains at least a portion of said at least one ingredient.

In some embodiments, the in-line heater is disposed within a distance in a range of about 15 mm to about 30 mm relative to the inlet port of the cell. In some embodiments, the in-line heater can be used to raise the temperature of the fluid up to about 60° C., e.g., in a range of about 25° C. to about 60° C. In some embodiments, the in-line heater can be implemented as a coil that wraps around a portion of a tubing through which the fluid is delivered from the fluid reservoir to the cell. A current source can apply a current to the coil to cause heating thereof, which can in turn heat up the fluid passing through the tubing.

In some embodiments, the system can further include two temperature sensors, one of which is disposed in proximity of an inlet port of the cell and the other is disposed in proximity of an outlet port of the cell for measuring the temperature of the fluid entering and exiting the cell. By way of example, in some embodiments, each of these sensors can be placed within about 15 mm to about 30 mm of any of the input and output port of the cell.

In some embodiments, the system can include a controller in communication with at least one of the temperature sensors to receive temperature data generated by the sensor. The controller can be configured to control the in-line heater in response to the received temperature data for adjusting temperature of the fluid entering the cell so as to achieve a fluid temperature within the cell that is substantially equal to a desired temperature. By way of example, in some such embodiments, the controller is configured to control the in-line heater so as to maintain the temperature of the fluid in the cell within +/−2 degrees of Celsius of a desired temperature.

The cell can include an outlet port (herein also referred to as output port) through which the fluid exits the cell. A return fluid path connects the output port of the cell to a return inlet port of the fluid reservoir to allow the fluid exiting the cell to return to the fluid reservoir. In this manner, a closed-loop fluid circulation path can be established between the fluid reservoir and the cell.

A pump can be coupled to the inlet fluid path connecting the fluid reservoir to the cell to facilitate the flow of the fluid between the reservoir and the cell. A variety of different pumps can be employed. By way of example, the pump can be a gear pump, a piston pump, a peristaltic pump, or any other suitable pump. In some embodiments, the pump and the cell are configured to provide fluid circulation between the fluid reservoir and the cell at a fluid flow rate greater than about 25 mL/min, e.g., in a range of about 25 mL/min to about 1 L/min.

In some embodiments, the inlet port of the cell is dimensioned such that the fluid enters the cell at a high flow velocity, e.g., at a flow velocity in a range of about 5.3 m/s to about 33.2 m/s. In some such embodiments, the maximum dimension of the cell's inlet port can be in a range of about 0.8 mm to about 2 mm.

In some embodiments, the inlet port of the cell is dimensioned such that the fluid enters the cell at a low flow velocity, e.g., at a flow velocity in a range of about 0.8 m/s to about 0.13 m/s. By way of example, in some such embodiments, a maximum dimension of the cell's inlet port can be in a range of about 0.8 to about 2 mm.

In some embodiments, a maximum dimension of the cell's outlet port is greater than a maximum dimension of the cell's inlet port. By way of example, a maximum dimension of the cell's outlet port can be in a range of about 2 mm to about 4 mm.

The fluid reservoir can include an outlet port through which fluid in the reservoir exits the reservoir to flow via an inlet fluid path, which connects the outlet port of the reservoir to the inlet port of the cell, to the cell. The fluid reservoir can further include a return inlet port for receiving the fluid exiting the cell via a return fluid path, which connects the outlet port of the cell to the return inlet port of the fluid reservoir. In some embodiments, the inlet port and the outlet port of the fluid reservoir are positioned at opposed ends thereof.

In some embodiments, a spray nozzle is coupled to the return inlet port of the fluid reservoir for providing a fluid stream directed at a wall of the reservoir for washing off residues, if any (such as ingredients extracted from the pharmaceutical dosage form), that are deposited on the reservoir wall.

In some embodiments, an ultraviolet spectrophotometer is coupled to the inlet fluid path, which extends from the outlet port of the fluid reservoir to the inlet port of the cell, for performing spectrophotometric analysis of the fluid flowing from the fluid reservoir to the cell. In some such embodiments, a bypass fluid path coupled to the fluid inlet path can be used to couple the spectrophotometer to the inlet fluid path. A valve can be disposed between the inlet fluid path and the bypass fluid path to which the spectrophotometer is coupled to control the flow of the fluid from the inlet fluid path to the spectrophotometer.

In some embodiments, an integrated stirring unit is disposed in proximity of the outlet port of the fluid reservoir for stirring the fluid as it exits the reservoir to be received by the cell. By way of example, in some embodiments, such an integrated magnetic stirring unit can include a magnetic element disposed in the fluid reservoir, e.g., in proximity of its outlet port, which can rotate under the influence of one or more external magnets to agitate the fluid.

In a related aspect, a system for controlled temporal extraction of ingredients of a pharmaceutical dosage form is disclosed, which comprises at least one fluid reservoir for storing a fluid comprising a solvent, a cell having an inlet port in fluid communication with the fluid reservoir for receiving a flow of the fluid from the reservoir and an outlet port through which the fluid can exit the cell, where the cell is configured to receive a pharmaceutical dosage form. A pump causes circulation of the fluid between the reservoir and the cell. The pump and the cell can be configured to allow introduction of the fluid into the cell at a flow rate greater than about 25 mL/min. The fluid flow over the pharmaceutical dosage form within the cell can cause extraction of one or more ingredients of the dosage form into the flowing fluid such that the fluid exiting the cell contains at least a portion of the ingredients.

In some embodiments, a maximum dimension of the cell's inlet port can be in a range of about 0.8 to about 2 mm. Further, in some embodiments, the cell's outlet port can have a maximum dimension that is greater than a maximum dimension of the cell's inlet port. An in-line heater can be disposed in proximity of the cell's inlet port for heating the fluid to an elevated temperature, e.g., a temperature in a range of about 40° C. to about 60° C., prior to entry into the cell. In some embodiments, the in-line heater is disposed within a distance in a range of about 15 mm to about 30 mm relative to the cell's inlet port.

Further, in some embodiments, the system can include a first temperature sensor disposed in proximity of the cell's inlet port for measuring the fluid temperature as it enters the cell and a second temperature sensor disposed in proximity of the cell's outlet port for measuring the fluid temperature as the fluid exits the cell. For example, each temperature sensor can be disposed within about 15 mm to about 30 mm of the cell's inlet or outlet port. A controller in communication with at least one of the temperature sensors, and preferably both temperature sensors, can receive temperature data from the sensor(s) and control the in-line heater in response to such temperature data to adjust the temperature of the fluid entering the cell so as to achieve a fluid temperature within the cell that is substantially equal to a desired temperature. For example, in some embodiments, the controller is configured to control the heater so as to maintain the temperature of the fluid in the cell within +/−2 degrees Celsius of a desired temperature.

In a related aspect, a system for controlled temporal extraction of ingredients of a pharmaceutical dosage form is disclosed, which comprises a plurality of controlled extraction units, each of which is configured to independently receive a pharmaceutical dosage form and each of which can include a fluid reservoir. The system can further include a controller in communication with the extraction units for controlling the operation thereof.

In some embodiments of the above system, each extraction unit comprises a cell having an inlet port in fluid communication with the reservoir for receiving a flow of the fluid from the reservoir and an outlet port through which the fluid can exit the cell, where the cell is configured for receiving a pharmaceutical dosage form. The fluid flow over the pharmaceutical dosage form disposed within the cell causes extraction of one or more ingredients thereof, e.g., via dissolution in the solvent.

In some embodiments, the inlet port of at least one of the cells has a maximum dimension in a range of about 0.8 mm to about 2 mm. In some embodiments, the inlet port of at least one of the cells is substantially circular and said maximum dimension corresponds to a diameter of the inlet port.

In some embodiments, at least one of the extraction units further comprises an in-line heater disposed in proximity of the inlet port of the cell associated with at least one extraction unit for heating the fluid to an elevated temperature prior to its entry into the cell, and a first temperature sensor disposed in proximity of the inlet port of the cell and a second temperature sensor disposed in proximity of the output port of the cell for measuring the temperature of the fluid entering and exiting the cell, respectively. In some embodiments, the heater causes the fluid temperature to rise to an elevated temperature, e.g., in a range of about 25° C. to about 60° C.

The controller is in communication with at least one of the temperature sensors to receive temperature data therefrom and is configured to control the in-line heater in response to the received temperature data for adjusting the temperature of the fluid entering the cell. Further, in some embodiments, the controller is capable of causing concurrent flow of the fluid to two or more of the extraction units.

Each of the extraction units can include a return fluid path for directing the fluid exiting the extraction unit to the fluid reservoir. In some embodiments, an inlet port of at least one of the cells has a maximum dimension in a range of about 0.8 mm to about 2.0 mm. Further, in some embodiments, an outlet port of at least one of the cells has a maximum dimension that is greater than a respective maximum dimension of an inlet port thereof. By way of example, a maximum dimension of the outlet port can be in a range of about 2 mm to about 4 mm.

Each of the multiple extraction units can include a pump, which can extract samples of the fluid contained in the respective fluid reservoirs of the extraction units for analysis. In some cases, the pump can be operated under the control of a controller for extracting the samples based on a predefined temporal schedule. In some embodiments, the extracted samples can pass through a filter to be received by a sample manager, which can direct the samples to an analysis module, such as a UV spectrophotometer and/or an LC column and/or an LC/MS analyzer.

In some embodiments, a multi-unit system according to the present teachings can receive one or more samples automatically from an automated sample introduction module. Such a system can further include a pump for automated extraction of samples of the fluid containing ingredients of one or more samples for spectral and/or chemical analysis.

In another aspect, an automated system for performing quality control of a pharmaceutical dosage form is disclosed, which includes a sample feeder for receiving a pharmaceutical dosage form and transferring the dosage form to a weight station at which the weight of the dosage form can be measured. Such transfer of the pharmaceutical dosage form can be achieved, for example, via a vibratory track. If the measured weight is not within an acceptable tolerance of an expected weight, the pharmaceutical dosage can be discarded. However, if the measured weight is within an acceptable tolerance of the expected weight, the pharmaceutical dosage form can be transferred, e.g., via a vibratory track, to a module in which a thickness of the pharmaceutical dosage form can be measured. In some embodiments, the pharmaceutical dosage form can then be automatically transferred, e.g., via a robotic arm, to a spectrometer (such as an NIR spectrometer) for measuring certain spectral features thereof. The pharmaceutical dosage form can then be transferred, e.g., via a robotic arm, to a sample introduction module, which can introduce the dosage form to a controlled extraction system according to an embodiment of the present teachings.

The extraction system can then be utilized, e.g., in a manner discussed above, to extract one or more ingredients of the pharmaceutical dosage form and the fluid within the system's fluid reservoir can be sampled, e.g., at predefined intervals, and the samples can be optionally transferred via a pump to a filter and from the filter to a sample manager, which can direct the sample to an analysis module (e.g., a UV/LC module) for spectral and/or chemical analysis. The analysis data can be transferred to a data storage unit for storage and analysis.

Further understanding of various aspects of the present teachings can be obtained by reference to the following detailed description in conjunction with the associated drawings, which are described briefly below.

DETAILED DESCRIPTION

Figure 1:
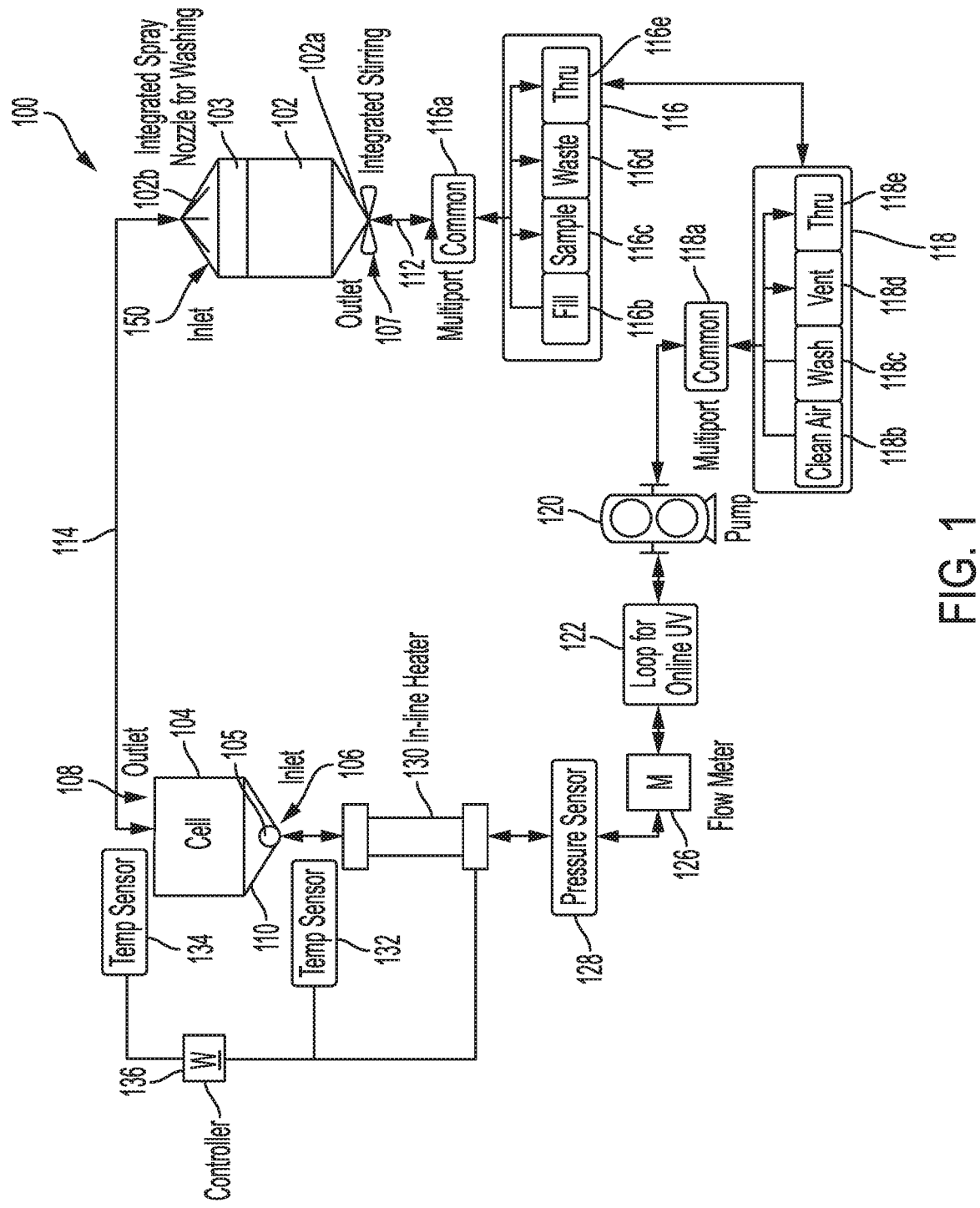
FIG. 1 schematically depicts a system according to an embodiment for controlled temporal extraction of ingredients of a pharmaceutical dosage form, FIG. 2 schematically depicts a cell used in embodiments of a system according to the present invention for receiving a pharmaceutical dosage form, FIG. 3 schematically depicts a bypass fluid loop in which a UV spectrophotometer is disposed, which can be optionally employed in the system depicted in FIG. 1 for in-situ spectral analysis of a fluid containing ingredients of the pharmaceutical dosage form as it circulates through the system, FIG. 4 schematically depicts an example of an implementation of an inline heater, which includes a coil wrapped around a portion of a tubing through which fluid is transferred to a cell holding a pharmaceutical dosage form, FIG. 5A schematically depicts an example of a controller including a feedback circuitry suitable for use in embodiments of the invention for adjusting temperature of the fluid entering the cell containing a pharmaceutical dosage form.

The present invention generally discloses methods and systems for controlled temporal extraction of ingredients of a pharmaceutical dosage form. In some embodiments, such a system can include, among other elements, a vessel (herein also referred to as a reservoir) for storing a fluid comprising a solvent suitable for extraction of the ingredients of the pharmaceutical dosage form (e.g., via dissolution in the solvent), a cell for holding the pharmaceutical dosage form, an inline heater for heating the fluid to a desired elevated temperature, and a pump for establishing a closed-loop circulation of the fluid from the vessel through the heater and the cell before returning to the vessel. As discussed in more detail below, in some embodiments, the return port of the vessel can include a spray nozzle for washing the vessel. In some embodiments, the vessel can be filled with a volume of extraction solvent in a range of about 50 mL to about 1 L. In some embodiments, the pump (e.g., a gear pump) can circulate the fluid at a flow rate of up to about 1 L/min and a flowmeter can be employed to monitor the flow rate. Further, as discussed in more detail below, a feedback system in communication with the flowmeter can be employed to control the flowrate at a user defined value.

The inline heater allows for rapid heating of the fluid to a temperature, e.g., up to about 60° C. In many embodiments, the inline heater is positioned directly below the cell in which the pharmaceutical dosage form is disposed so as to quickly heat the fluid and further reduce heat loss between the heater and the cell. As discussed in more detail below, the temperature of the fluid is monitored directly below and above the cell and the temperature readings are employed by a controller to modulate the temperature of the inline heater so as to control the fluid temperature within the cell.

The cell in which the pharmaceutical dosage form is disposed includes an inlet port for receiving the fluid and an outlet port through which the fluid exits the cell. In some embodiments, the cell's inlet orifice (herein also referred to as the inlet port) can have a size (e.g., a diameter) in a range of about 1 mm to about 1.5 mm, though other sizes can also be employed. The outlet orifice (herein also referred to as the outlet port) is typically larger than the inlet port. In many embodiments, the sizes of the inlet and the outlet orifices are chosen so as to allow the highest amount of flow and backpressure that the pump can handle. This can in turn allow for a strong stream of fluid to enter the cell and impact the pharmaceutical dosage form. In some embodiments, an ultraviolet (UV) spectrophotometer can be placed in-line for monitoring of the fluid during extraction.

As discussed in more detail below, in some embodiments, multiple extraction units (herein also referred to as extraction modules) can be employed. A controller can be employed to control the extraction units so as to allow operating the extraction units independently or in parallel (e.g., for faster processing of multiple pharmaceutical dosage forms). In some embodiments, the controller can be housed in one of the extraction units. In some such embodiments, the controller can be removed from one extraction unit (e.g., in case of failure of that extraction unit) and be placed into another to continue the operation of the system.

As system according to the present teachings can include valves that can allow, for example, controlled filling of the vessel with a solvent and extraction of fluid sample(s) from the vessel for storage/analysis. The valve can also be used to pull in wash solvent, drain the fluid contained in the vessel, and/or pull in clean dry air to dry the system. This allows the system to be modular and used as an independent extraction system or in conjunction with other modules for semi or fully automated operation.

In a fully automated configuration, the system can be coupled with other elements to provide, for example, fully automated testing of a pharmaceutical dosage form (e.g., from tablet press to data analysis). Such a fully automated system can be used, for example, for complete destructive testing of pharmaceutical dosage forms to facilitate the continuous manufacturing of pharmaceutical dosage forms.

Various terms are used herein in accordance with their ordinary meanings in the art. The term "about" as used herein to denote +/−10 percent variation in a numerical value.

FIG. 1 schematically depicts a system 100 for controlled temporal extraction of ingredients of a pharmaceutical dosage form. The system 100 includes a fluid reservoir 102 for storing a fluid 103 comprising a solvent for extracting one or more ingredients of a pharmaceutical dosage form as well as for receiving a mixture (e.g., a solution) of the solvent and the extracted ingredient(s) in a closed-loop fashion, as discussed in more detail below. A variety of solvents can be employed in the practice of the present teachings. Some examples of such solvents include, without limitation, acetonitrile, ethanol, and methanol.

The system 100 further includes a cell 104 for receiving a pharmaceutical dosage form 105, e.g., a tablet. In this embodiment, the cell 104 includes an input port 106 (herein also referred to an inlet port) for receiving fluid and an output port 108 (herein also referred to as an outlet port) through which the fluid can exit the cell. The outlet port can be removably and replaceably coupled to the cell (e.g., via a spring-loaded mechanism) to allow introduction of a pharmaceutical dosage form into the cell. In this embodiment, a pharmaceutical dosage form can be placed at the bottom of the cell in proximity of the inlet port. As discussed in more detail below, in this embodiment, the bottom of the cell can have an inverted conical structure having an angle suitable for supporting the pharmaceutical dosage form placed in proximity of the vertex of the cone, as shown schematically in FIG. 1.

Figure 2:
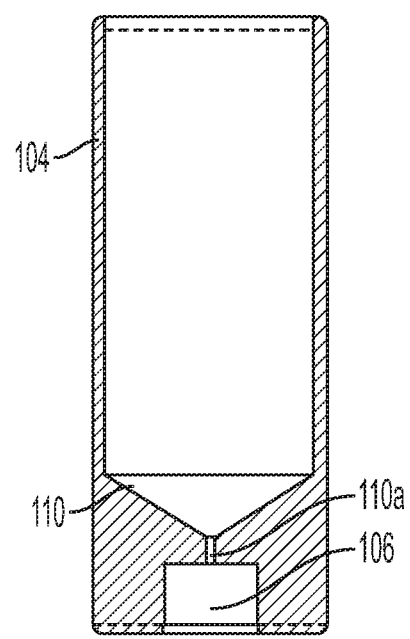

With reference to FIG. 2, the mount 110 includes an opening 110a at its vertex that is in fluid communication with the inlet port of the cell so as to allow a flow of the fluid over the pharmaceutical dosage form placed in the cell.

Referring again to FIG. 1, the fluid reservoir 102 includes an outlet (exit) port 102a through which the fluid in the reservoir exits to reach the cell 104. More specifically, an inlet fluid conduit 112 is fluidly coupled at a proximal end 112a thereof to the exit port 102a of the fluid reservoir 102 to receive the fluid exiting the reservoir. As discussed in more detail below, an integrated magnetic stirring mechanism 107 is coupled to the outlet port of the fluid reservoir to agitate the fluid as it leaves the fluid reservoir.

The fluid exiting the cell 104 returns to the reservoir 102 via a return fluid path 114 that extends from an output port 108 of the cell to an input port 102b of the fluid reservoir. As shown in FIG. 1, the outlet port 102a of the fluid reservoir 102 is fluidly coupled to a multiport manifold 116 that includes a common manifold 116a that can selectively direct the fluid received from the fluid reservoir to one of four ports 116b, 116c, 116d, and 116e, which are herein labeled, respectively, fill, sample, waste, and Thru ports, and which will be described in more detail below.

In this embodiment, the Thru port 116e can be used to direct the fluid exiting the fluid reservoir 102 to the cell 104 in which the pharmaceutical dosage form is disposed. Specifically, the illustrated system 100 includes another multiport manifold 118 that includes a common manifold 118a that can selectively communicate with a plurality of ports 118b, 118c, 118d, and 118e, which are herein labeled, respectively, Clean Air, Wash, Vent, and Thru, and which will be described in more detail below.

The Thru port 116e of the multiport manifold 116 is fluidly coupled to the Thru port 118e of the multiport manifold 118. The fluid received by the Thru port 116e is transferred to the Thru port 118e and reaches, via the common manifold 118a, a pump 120, which facilitates the circulation of the fluid between the fluid reservoir 102 and the cell 104. A variety of pumps can be used in the practice of the present teachings. Some examples of suitable pumps include, without limitation, a gear pump, a piston pump, or a peristaltic pump, among others.

Figure 3:
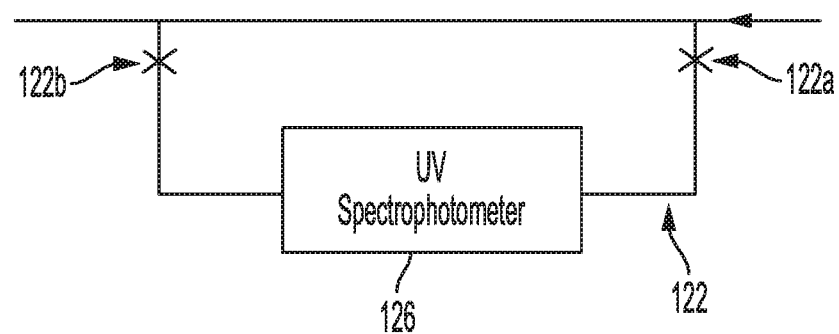

With reference to FIG. 1 as well as FIG. 3, a bypass loop 122 can be optionally utilized to couple an ultraviolet spectrophotometer 126 to the fluid inlet path extending between the outlet 102a of the fluid reservoir and the inlet 106 of the cell 104. In this embodiment, the bypass loop 122 includes two valves 122a and 122b, which can be used to direct a portion of the fluid received from the fluid reservoir 102. The bypass loop 122 can allow a portion of the fluid flowing through the fluid inlet path to be directed to the spectrophotometer for in-situ measurement of selected properties of the fluid. By measuring the absorbance of the solution versus a standard preparation, the concentration of the solution can be determined in order to calculate % of the active pharmaceutical ingredient in solution at the specific timepoint. In other embodiments, the system may not include such a spectrophotometer.

In this embodiment, a flow meter 126 and a pressure sensor 128 are disposed between the bypass loop 122 and an in-line heater 130 for measuring the flow rate of the fluid and the fluid's pressure, respectively. A variety of flow meters and pressure sensors can be employed. By way of example, a flow meter marketed by IFM under the trade designation SM4000 and a pressure sensor marketed by Honeywell under the trade designation 19 mm Series Heavy Duty Pressure Transducer can be employed.

With continued reference to FIG. 1, in this embodiment, the in-line heater 130 is coupled to the inlet fluid path in proximity of the inlet port 106 of the cell 104. The in-line heater 130 can heat the fluid within the inlet fluid path prior to its entry into the cell. The in-line heater 130 is typically placed sufficiently close to the inlet port 106 of the cell 104 so as to minimize any heat loss suffered by the fluid as it flows between the location at which the in-line heater is placed and the cell's input port. By way of example, in some embodiments, the in-line heater 130 is placed within about 15 mm to about 30 mm of the inlet port of the cell.

In this embodiment, the in-line heater 130 is employed to raise the temperature of the fluid up to about 60° C. as it enters the cell 104. By way of example, in some embodiments, the in-line heater 130 can be employed to raise the temperature of the fluid to an elevated temperature in a range of about 25° C. to about 60° C.

Figure 4:
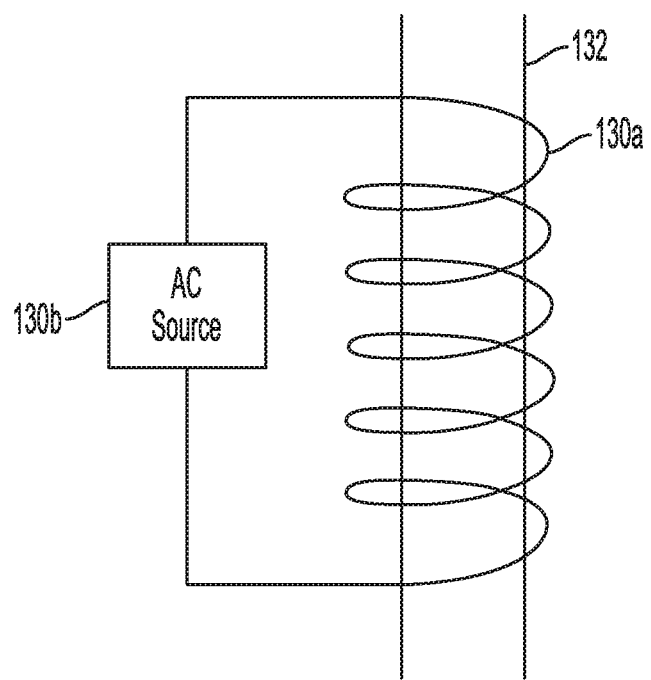

The in-line heater 130 can be implemented in a variety of different ways. By way of example, as shown schematically in FIG. 4, the in-line heater can be in the form of a coil 130a that is wrapped around a portion of a tubing 132 through which the fluid flows to the cell 104. A current source 130b can apply a current to the coil to heat up the coil and consequently the fluid flowing through the tubing 132. A variety of commercially available heaters can be employed in the practice of the present teachings. For example, a heater marketed by Watlow under the trade designation Fluent In-line Heater can be utilized. The placement of the in-line heater 130 in close proximity to the inlet port 106 of the cell '104 can advantageously minimize heat loss suffered by the heated fluid as it propagates from the heater to the cell.

In this embodiment, a temperature sensor 132 is disposed between the in-line heater 130 and the input port 106 of the cell 104 as close to the inlet port 106 of the cell as practicable to measure the temperature of the fluid as it enters the cell. By way of example, in some embodiments, the temperature sensor 132 can be placed within about 15 mm to about 30 mm of the inlet port of the cell 104.

Another temperature sensor 134 is placed in proximity of the outlet port 108 of the cell 104 to measure the temperature of the fluid as it exits the cell. The temperature sensor 134 is positioned as close to the outlet port of the cell 104 as practicable so as to ensure accurate measurement of the fluid as it exits the cell. In some embodiments, an average of the fluid temperatures measured by the temperature sensors 132 and 134 can be used as a measure of the fluid temperature within the cell.

The system 100 further includes a controller 136 that is in electrical communication with the temperature sensors 132 and 134 to receive temperature data generated by those sensors. The controller 136 is also in electrical communication with the in-line heater 130. Specifically, the controller receives the temperature data generated by the temperature sensors 132 and 134 and compares the measured fluid temperature (e.g., an average of the temperature readings of the two sensors) with a pre-defined desired temperature (herein also referred to as predefined set point temperature). If the measured fluid temperature is within an acceptable tolerance of the desired temperature, e.g., within about +/−2° C., the controller takes no action. However, if the deviation between the measured fluid temperature and the desired fluid temperature exceeds the acceptable tolerance, the controller can control the in-line heater 130 so as to adjust the temperature of the fluid entering the cell. For example, if the measured temperature is less than the desired temperature by a value more than the acceptable tolerance, the controller can adjust the setting of the in-line heater 130 to increase the temperature of the fluid. For example, the controller can communicate with a current source supplying current to the heater to increase the current applied to the heater so as to provide additional heating to the fluid, thereby increasing its temperature.

Alternatively, if the measured fluid temperature is greater than the desired temperature by a value exceeding the acceptable tolerance, the controller can control the in-line heater to lower the heat delivered to the fluid, thereby reducing its temperature. In other words, the controller controls the temperature of the fluid within the cell via a closed-loop feedback based on the temperature readings of the sensors 132 and 134.

Figure 5A:
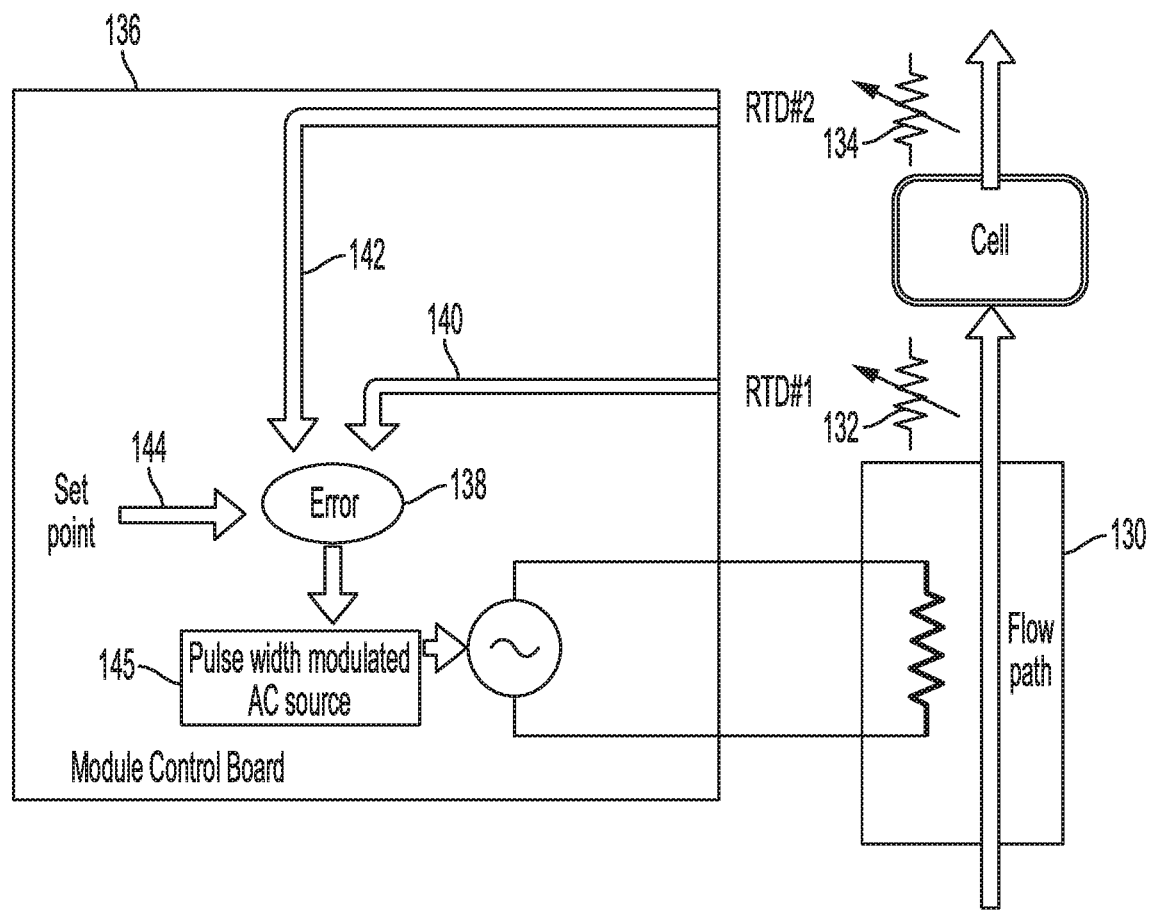
FIG. 5B is a flow chart depicting various steps in one embodiment for use in a system according to the invention for controlling the temperature of a fluid within a cell of the system containing a pharmaceutical dosage form, FIG. 6 schematically depicts an integrated magnetic stirrer disposed in the outlet of a fluid reservoir of a system according to the certain embodiments of the invention for agitating the fluid, FIG. 7 schematically depicts the use of a vent port in a system according to an embodiment for venting the system, FIG. 8 schematically depicts an LC/MS system suitable for performing chemical analysis of a fluid in which ingredients of a pharmaceutical dosage form is dissolved in accordance with the teachings of the invention, FIG. 9 schematically depicts the use of waste port in an embodiment of a system according to the invention for draining the fluid contained in the system's fluid reservoir, FIG. 10 schematically depicts the use of fill port in an embodiment of a system according to the invention for filling the system's fluid reservoir with a solvent suitable for extracting ingredients of a pharmaceutical dosage form, FIG. 11 schematically depicts a system according to an embodiment of the invention, which unlike the system depicted in FIG. 1, does not include an inline UV spectrophotometer, FIG. 12 schematically depicts the operation of a system according to an embodiment with the pump providing a reverse flow of the circulating fluid between the cell containing the pharmaceutical dosage form and the fluid reservoir, FIG. 13A schematically depicts a feedback controller suitable for controlling the flow rate of the fluid through an embodiment of a system according to the present invention.
Figure 5B:
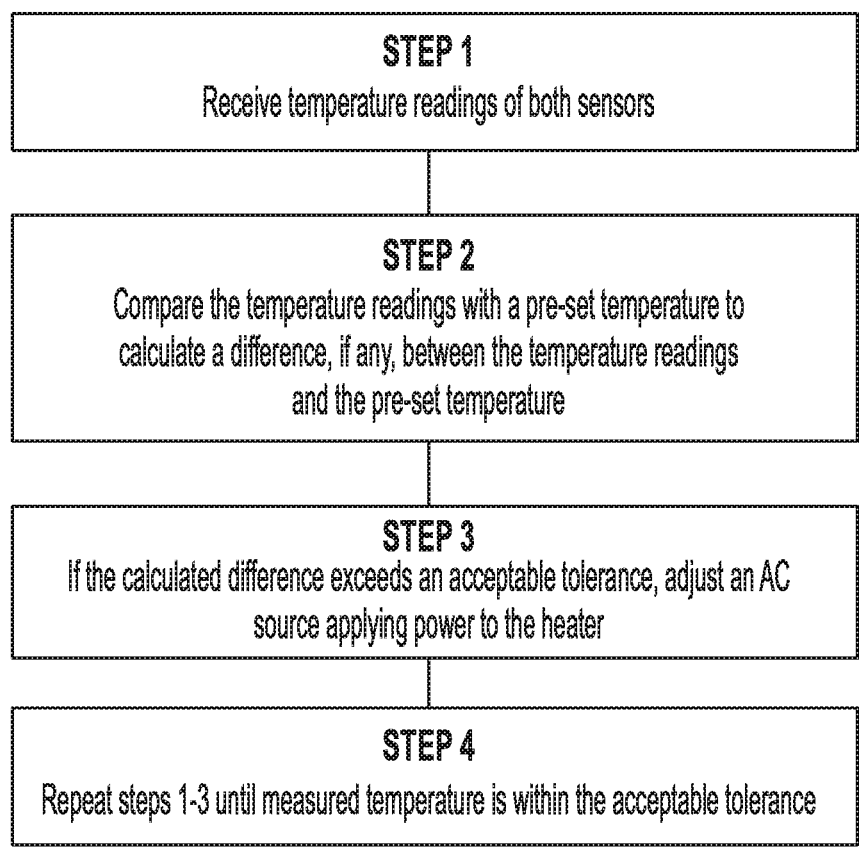

With reference to FIGS. 5A and 5B, an example of an implementation of the controller 136 includes circuitry (not shown) for receiving temperature data from the temperature sensors 132 and 134. In some embodiments, the temperature sensors 132 and 134 can be temperature sensitive resistors (thermistors), which exhibit a change in their electrical resistance as a function of temperature. The controller can include standard circuitry for measuring the electrical resistances of these thermistors, thereby determining the temperature of the fluid measured by the sensors. The controller can include an error circuitry 138, which receives the temperature readings 140 and 142 from the temperature sensors 132 and 134, respectively, at two inputs thereof. Further, the error circuitry 138 receives a reference temperature 144 (herein also referred to as the set point temperature or desired temperature) at another input thereof. The error circuitry 138 compares the received temperature readings 140 and 142 with the set point temperature 144 to determine whether an adjustment of the current applied to the in-line heater 130 is required. In some embodiments, the error circuitry can determine that an adjustment of the current applied to the in-line heater 130 is needed if any of the temperature readings 142 and 140 deviates from the set point temperature 144 by more than a pre-defined tolerance (e.g., +/−2 degrees). In other embodiments, the error circuity 138 can compare an average of the temperature readings 140 and 142 with the set point temperature to determine whether an adjustment of the current applied to the in-line heater 130 is required.

If the error circuitry 138 determines that an adjustment of the heat applied to the fluid via the in-line heater is required, it can provide a signal to a current source supplying a current to the in-line heater to adjust the current applied to the in-line heater. In this illustrated embodiment, the current source is a pulse width modulated AC voltage source 145. The error circuitry can apply a control signal to the voltage source 145 for adjusting the duty cycle of the power it applies to the in-line heater 130, thereby adjusting the average current applied to the in-line heater and hence the heat supplied to the fluid passing therethrough. For example, if the error circuitry determines that the temperature of the fluid should be increased, it can apply a control signal to the AC voltage source to increase the duty cycle of the power applied to the in-line heater, and if the error circuitry determines that the temperature of the fluid should be decreased, it can apply a control signal to the AC voltage source to lower the duty cycle of the power applied to the in-line heater.

This process is iterated until the error between the measured temperatures and the preset point is within an acceptable predefined tolerance (e.g., +/−2 degrees).

The error circuitry 138 can be implemented in a manner known in the art. For example, one or more differential amplifiers can be employed for comparison of the temperature readings with the set point temperature and other known components and methods, such as transistors, switches, etc., can be employed in a manner known in the art to use the output of the error circuitry for controlling the AC voltage source providing power to the in-line heater.

Referring again to FIG. 1, as discussed above, the pump 120 establishes a closed-loop fluid circulation between the fluid reservoir 102 and the cell 104 in which the pharmaceutical dosage form is disposed. In this embodiment, the fluid reservoir 102 includes a spray nozzle 150 that is integrated within the fluid reservoir 102 and is coupled to its fluid return inlet port 102b. The integrated spray nozzle 150 sprays the returning fluid entering the fluid reservoir 102 via the return inlet port 102b as a fluid stream onto an inner wall of the fluid reservoir. The fluid stream can advantageously wash off residues, if any, such as residues containing ingredients extracted from the pharmaceutical dosage form, from the inner wall of the fluid reservoir, thereby ensuring that the concentration of the ingredients in the fluid contained within the fluid reservoir is an accurate reflection of the concentration of the ingredients in the pharmaceutical dosage form.

Figure 6:
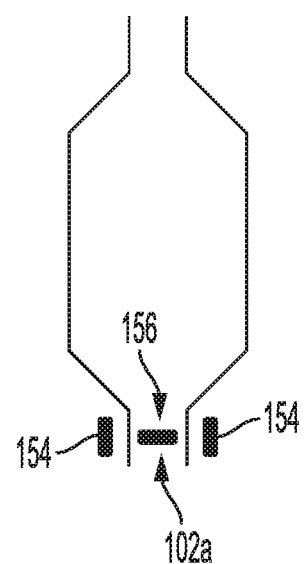

With continued reference to FIG. 1, the system 100 further includes an integrated stirring system 152 that is coupled to the outlet port 112a of the fluid reservoir 102 that can stir the fluid as it exits the fluid reservoir. As shown schematically in FIG. 6, the integrated stirring system 152 can include a plurality of magnets 154 disposed outside the wall of the outlet port 102a of the fluid reservoir 102, which can be rotated to spin a stir bar 156 placed inside the outlet port 112a, thereby agitating the fluid exiting the fluid reservoir.

Figure 7:
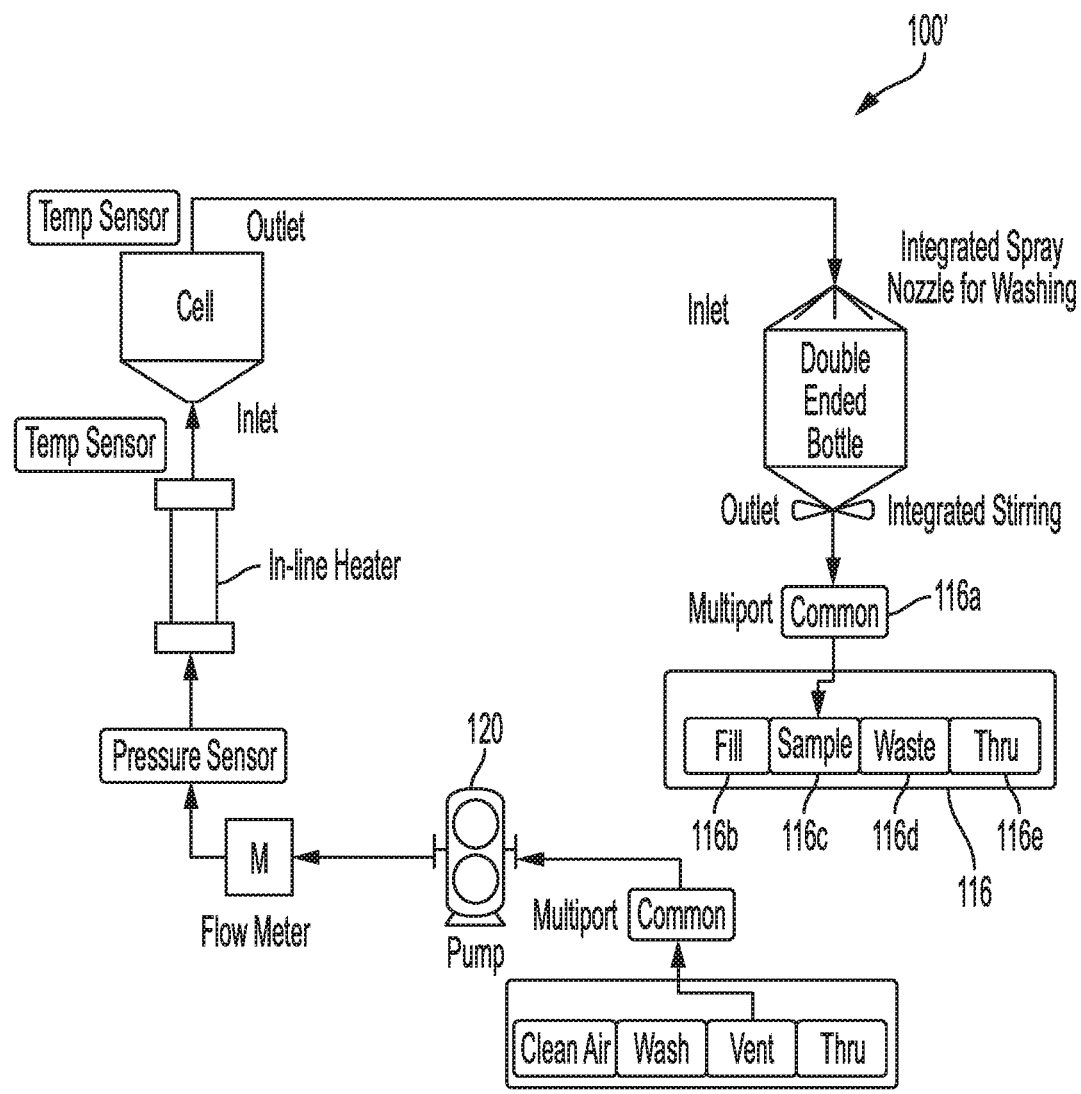

As noted above, in some embodiments, the closed-loop flow of the fluid between the fluid reservoir and the cell holding the pharmaceutical dosage form can be periodically interrupted, e.g., every 2, 4, or 6 hours, to extract a sample of the fluid within the fluid reservoir for analysis. For example, as shown in FIG. 7, the common port 116a of the multiport manifold 116 can be employed to switch the flow of the fluid exiting the fluid reservoir from the Thru port 116e to the sample port 116c, through which a sample of the fluid contained within the fluid reservoir can be obtained. In other words, the fluid exiting the fluid reservoir can be redirected from circulating to the cell 104 to the sample port 116c and a sample of the fluid can be collected from the sample port 116c.

Figure 8:
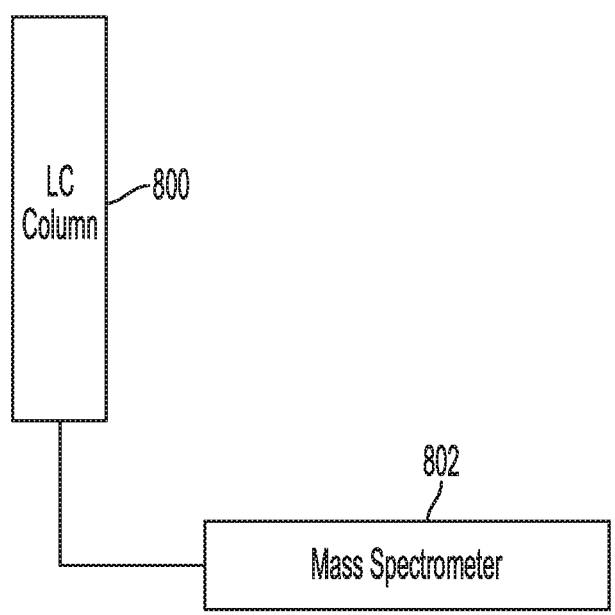
Figure 9:
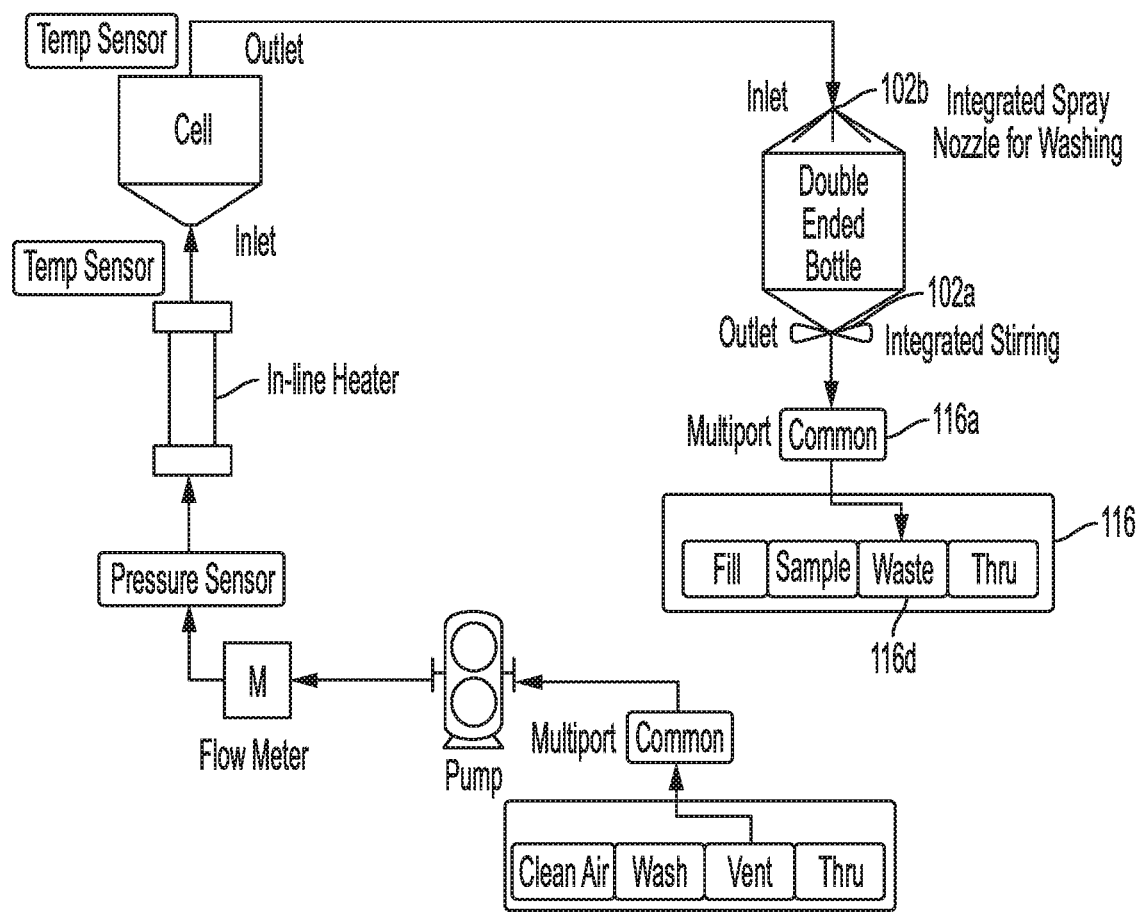

In some embodiments, the fluid sample can be subjected to liquid chromatography-mass spectrometry (LC-MS) analysis to determine the concentrations of the ingredients of the pharmaceutical dosage form dissolved in the solvent. By way of example, FIG. 8 schematically depicts such an LC-MS system, which includes an LC column 800 configured to receive the fluid sample and a tandem MS-MS mass analyzer 802 that is coupled to the LC column for receiving the eluents exiting the LC column and determining their mass-to-charge ratios in a manner known in the art. Other analysis modalities can also be applied to the fluid sample extracted from the fluid reservoir. Some examples of such modalities include, without limitation, ultraviolet, infrared and near-infrared spectrometry With reference to FIG. 9, the common manifold 116a of the multi-port manifold 116 can be employed to connect the outlet 102a of the fluid reservoir 102 to the waste port 116d so as to drain the fluid contained within the fluid reservoir.

Figure 10:
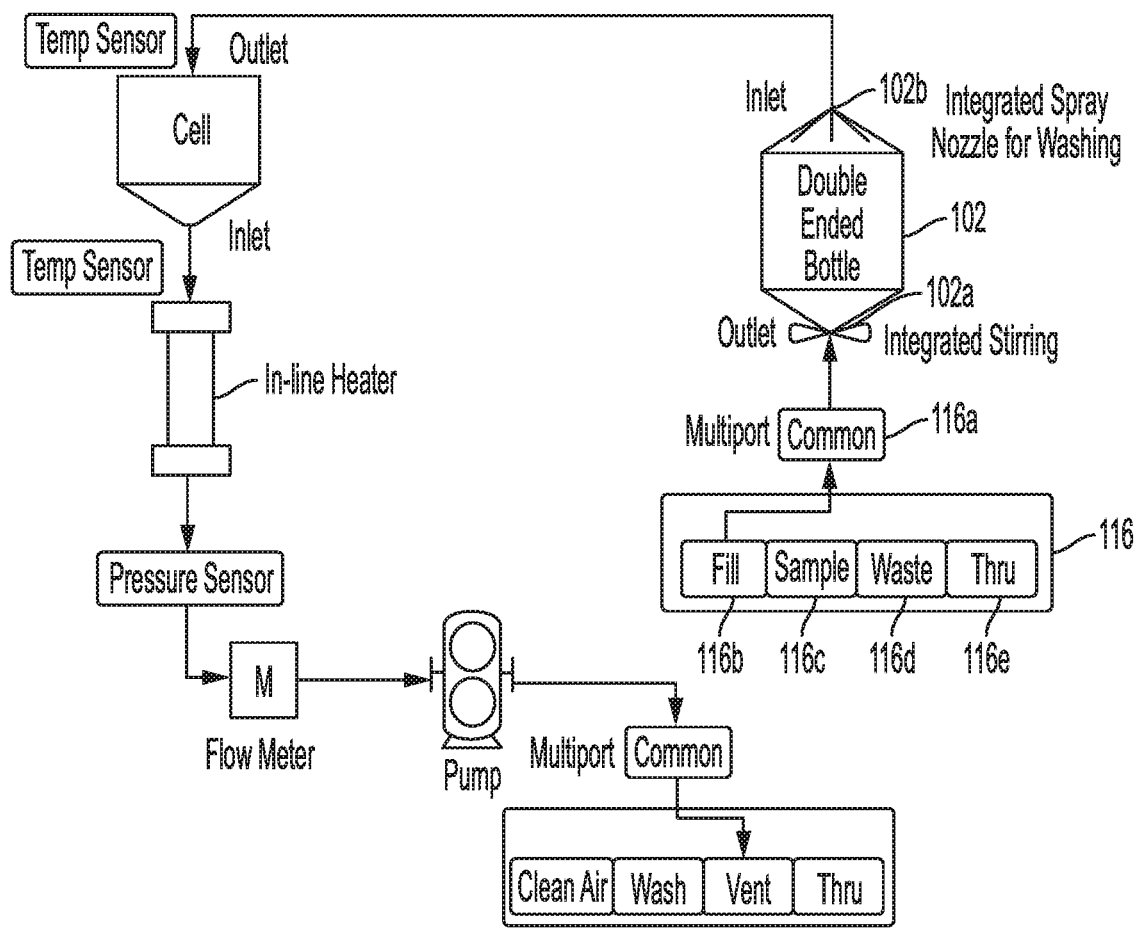

Further, with reference to FIG. 10, the common manifold 116a of the multi-port manifold 116 can connect the outlet port 102a of the fluid reservoir 102 to the fill port 116b to allow filling the fluid reservoir 102 with a solvent for use in extracting one or more ingredients of a pharmaceutical dosage form disposed in the cell 104.

Figure 11:
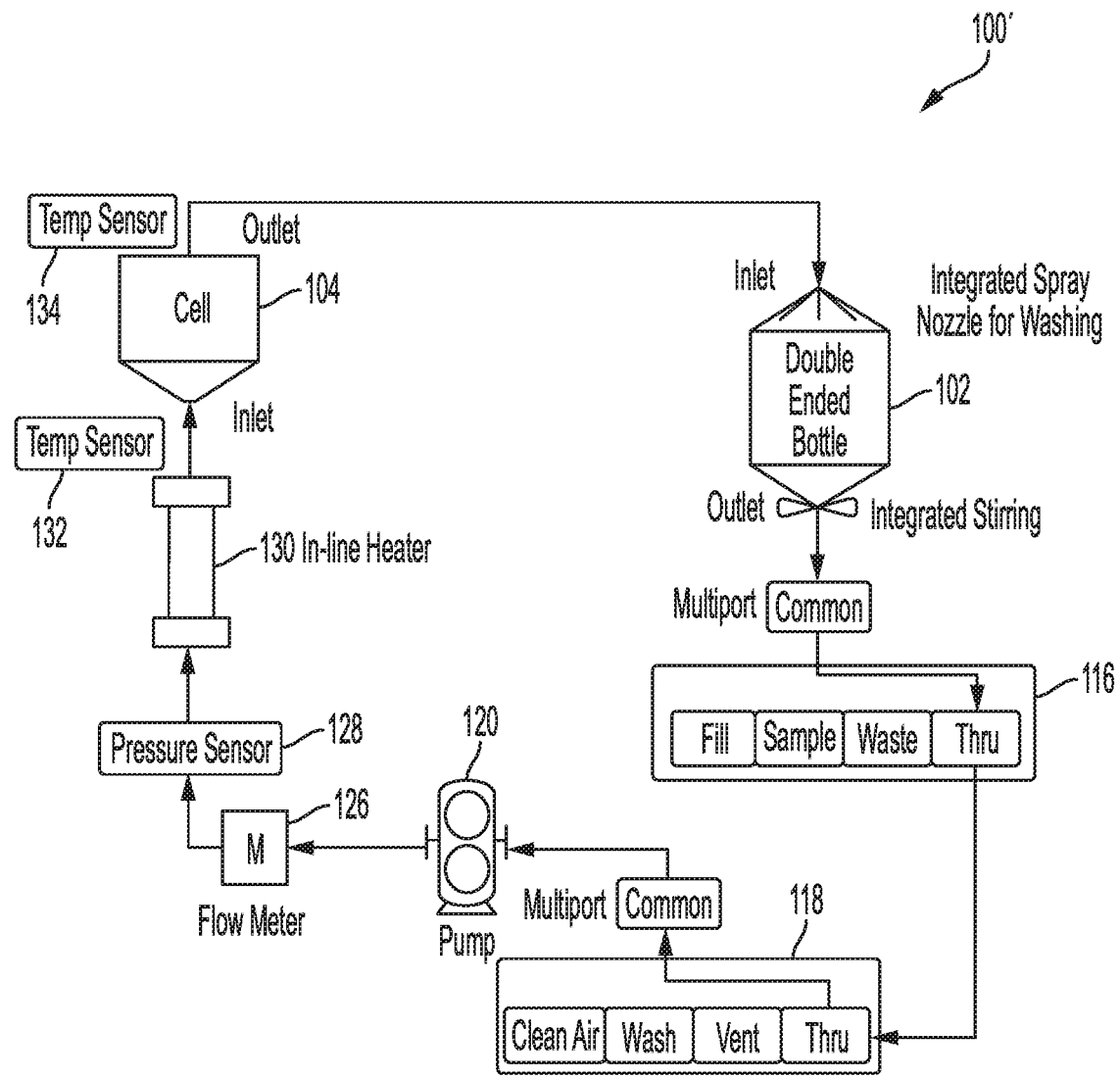

Although in the above system 100 a spectrophotometer is utilized, FIG. 11 depicts an embodiment 100' of a system according to the present teachings for extracting one or more ingredients of a pharmaceutical dosage form, which is similar to the system 100 in all respects except that the system 100' does not include a spectrophotometer coupled to the inlet fluid path connecting the fluid reservoir 102 to the cell 104 in which the pharmaceutical dosage form is placed.

Figure 12:
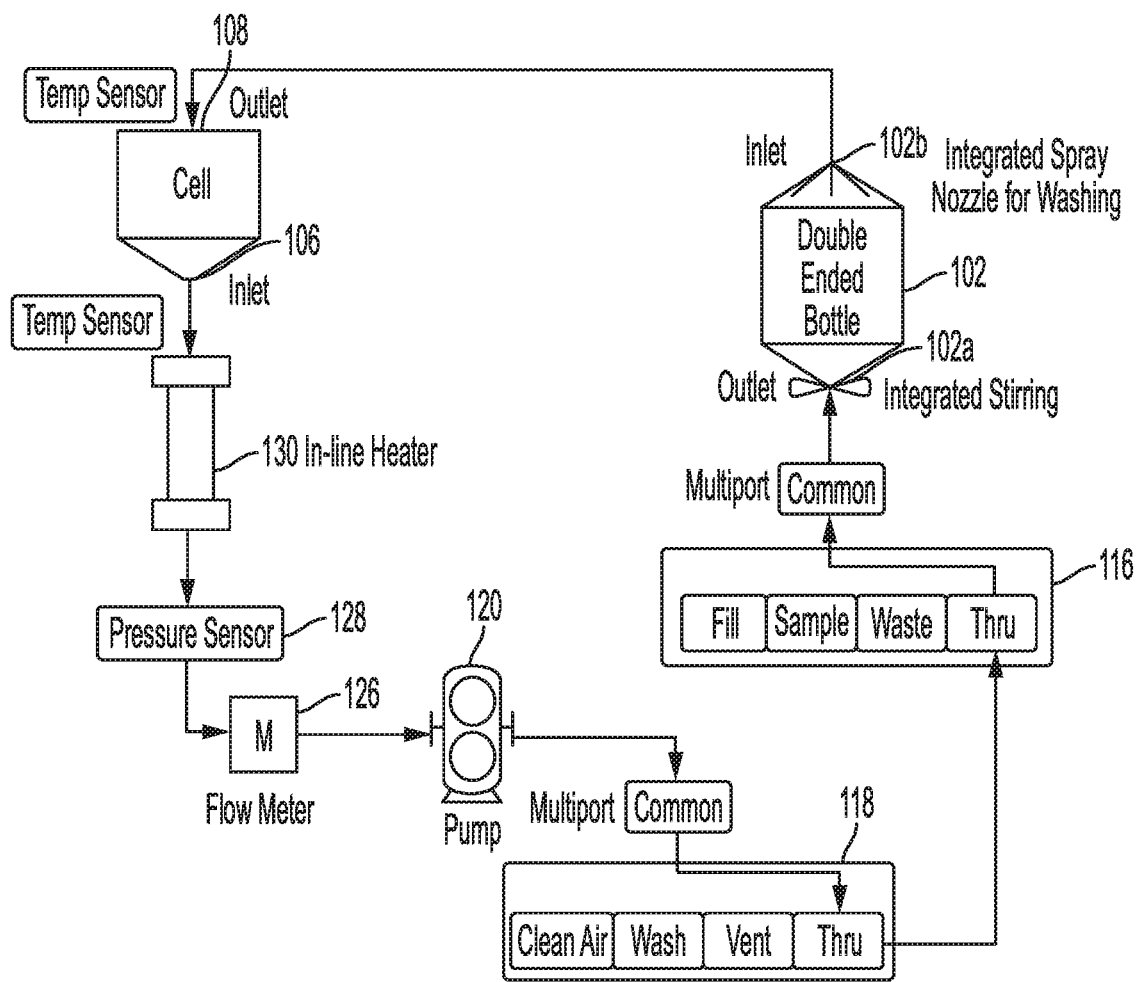

With reference to FIG. 12, the pump 120 can be operated in a reverse direction to reverse the circulation of the fluid between the fluid reservoir 102 and the cell 104 such that the fluid leaves the fluid reservoir 102 via the inlet port 102b to be received by the cell 104 via the outlet port 108 (which is functioning as an inlet port in this embodiment). The fluid leaving the cell can then exit the cell via its inlet port 106 (which is functioning as an outlet port in this embodiment) to return to the fluid reservoir 102 via passage through the in-line heater 130, the pressure sensor 128, the flow meter 126, the pump 120, the multi-port manifold 118, and the multi-port manifold 116. This allows for the internal plumbing to be drained so that all the media is back in the bottle for sampling. It also presents an empty system for easier cleaning and cell removal.

Figure 13A:
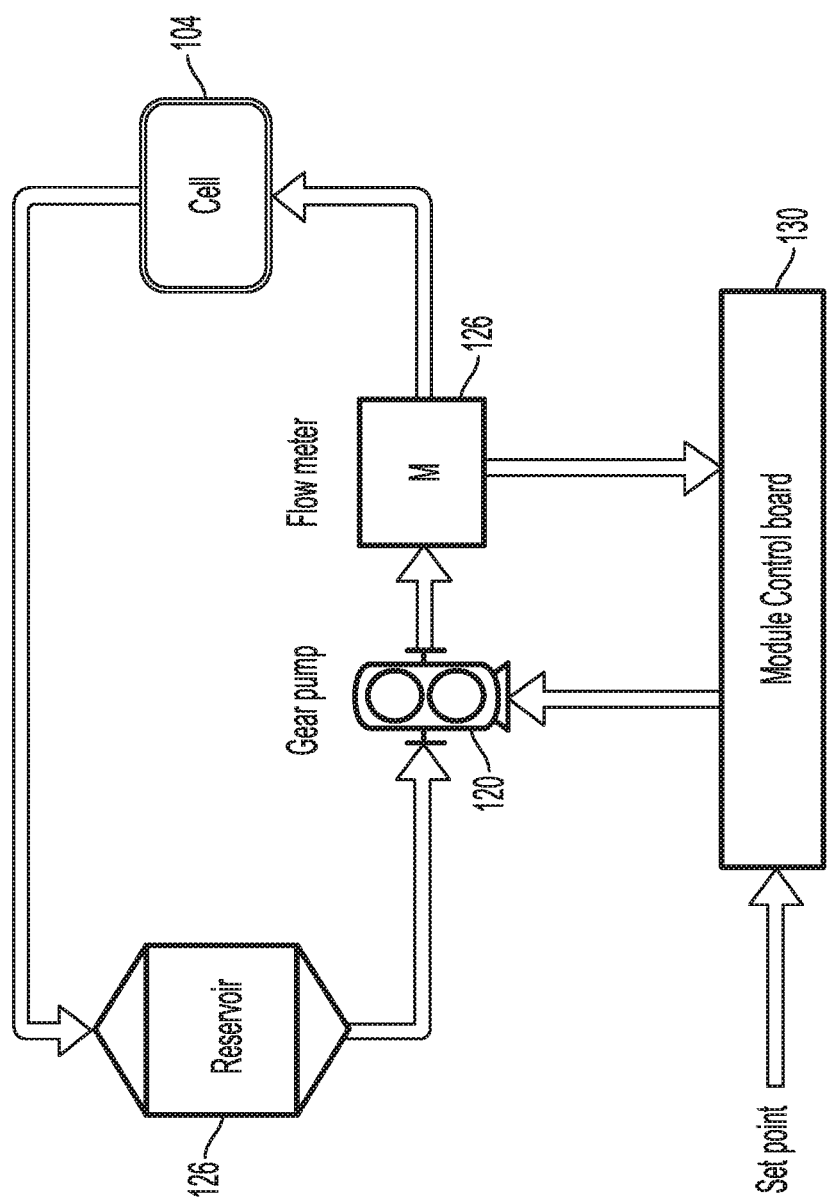
FIG. 13B is a flow chart that depicts various steps in a method for controlling flow rate of the fluid in an embodiment of a system according to the present invention, FIG. 13C schematically depicts an example of an implementation of the feedback controller depicted in FIG. 13A, FIG. 14 schematically depicts a system for controlled temporal extraction of ingredients of a pharmaceutical dosage form having multiple extraction units, FIG. 15 schematically depicts a system for controlled temporal extraction of ingredients of a pharmaceutical dosage form having multiple extraction units and capable of being operated in a semi-automatic fashion, FIG. 16 schematically depicts a system for controlled temporal extraction of ingredients of a pharmaceutical dosage form having multiple extraction units and capable of being operated in a fully automatic fashion, FIG. 17 schematically depicts an automated quality control system for testing a pharmaceutical dosage form according to an embodiment of the present invention, and FIG. 18 schematically depicts an example of an implementation of a controller suitable for use in various embodiments of the invention.
Figure 13B:
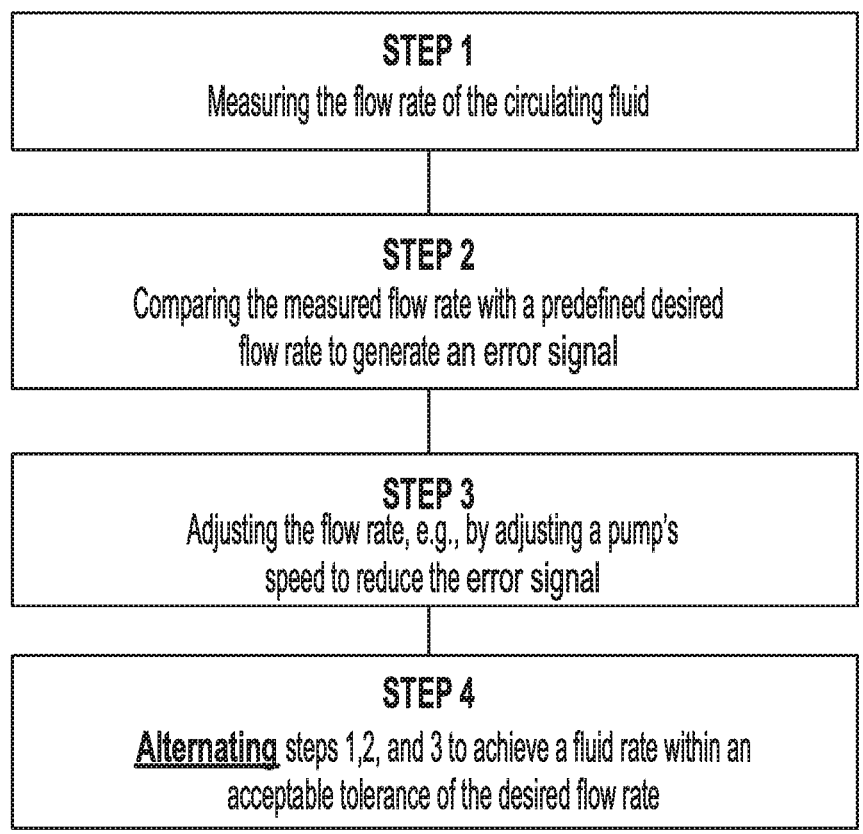
Figure 13C:
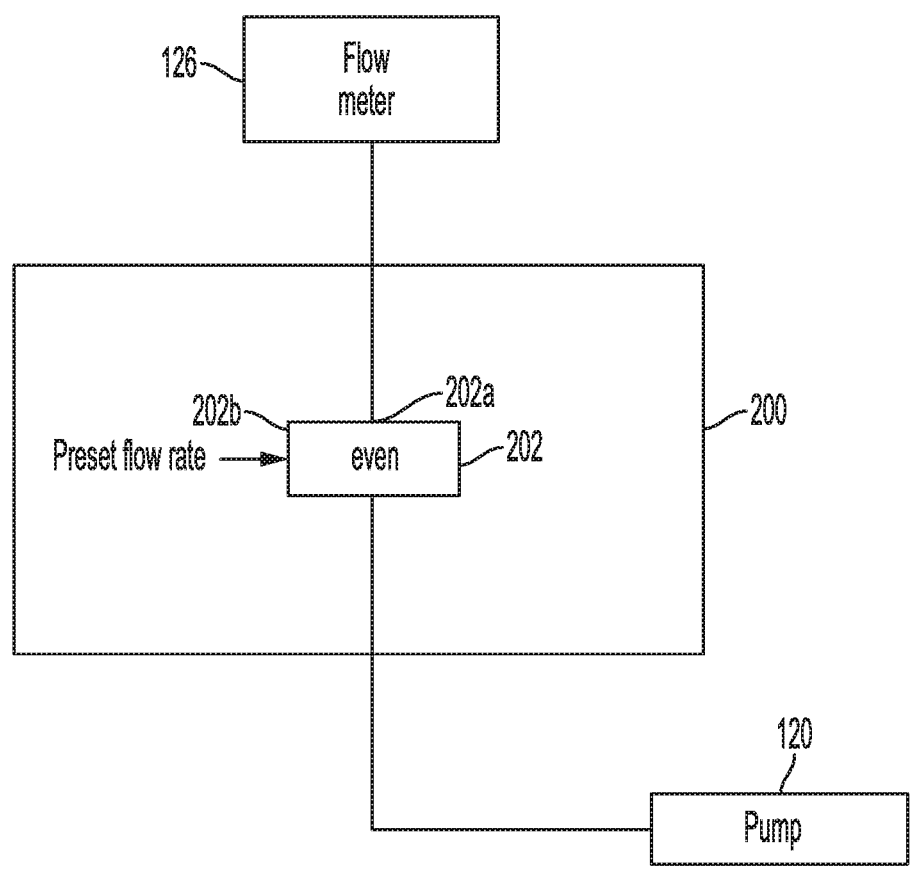

In some embodiments, a controller can be employed to adjust the flow rate of the fluid circulating between the fluid reservoir 102 and the cell 104. For example, with reference to FIGS. 13A and 13B, an implementation of a system for controlling the flow rate of the fluid includes a control module 200 that is in communication with the flow meter 126 to receive data regarding the flow rate of the circulating fluid therefrom. The control module is also in communication with the pump 120 to adjust the pumping speed of the pump based on the flow rate data received from the flow meter 126. In particular, as shown schematically in FIG. 13C, the control module 200 can include an error circuitry 202 that receives the measured flow rate from the flow meter 126 at one input 202a thereof and receives a predefined (preset) flow rate at another input 202b thereof. The error circuitry compares the two input values and applies an appropriate signal to the pump 120 based on that comparison. For example, if the comparison of the measured flow rate and the predefined flow rate shows that the measured flow rate exceeds the predefined flow rate more than an acceptable tolerance, the error circuitry can apply a control signal to the pump 120 to lower the speed of the pump and hence the flow rate of the circulating fluid. Alternatively, if the comparison of the measured flow rate and the predefined flow rate shows that the measured flow rate is less than the predefined flow rate more than an acceptable tolerance, the error circuitry can apply a control signal to the pump 120 to increase the pump speed, thereby adjusting the flow rate. This process is iterated until the measured fluid flow rate is within an acceptable tolerance of the predefined desired flow rate. Similar to the controller 136, the error circuitry can be implemented using standard components and methods, such as differential amplifiers, resistors, etc.

The above system can used to determine the controlled release of a variety of different pharmaceutical dosage forms, such as, tablets, capsules, creams, ointments, parenterals, powders, and API's.

Figure 14:
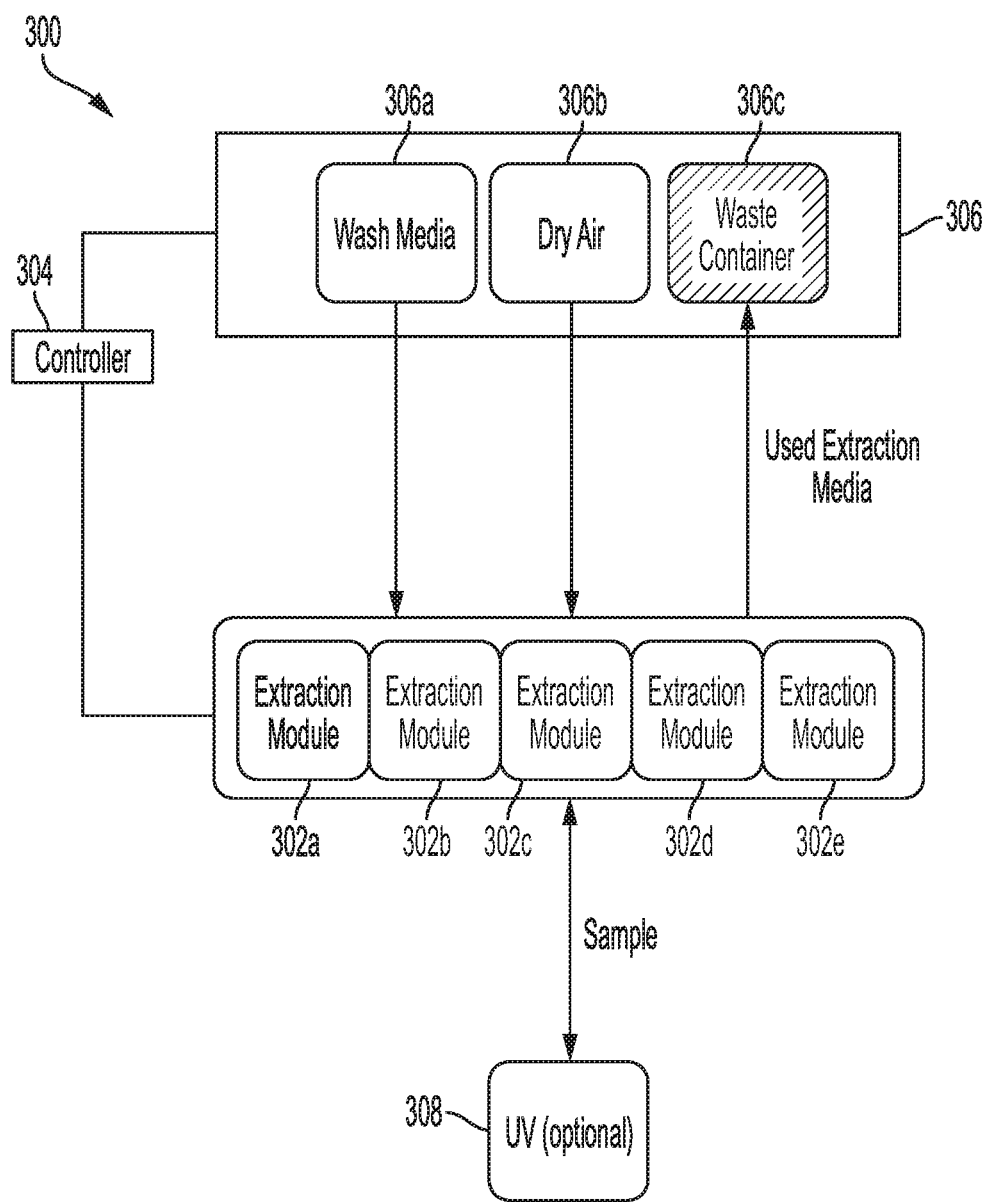

In a related aspect, a system for controlled temporal extraction of ingredient(s) of a pharmaceutical dosage form is disclosed, which includes multiple extraction units. By way of example, FIG. 14 schematically depicts such a system 300, which includes a plurality of extraction modules (herein also referred to as extraction units) 302a, 302b, 302c, 302d, and 302e (herein referred to as extraction modules 302), which can be run in parallel under control of a controller 304.

In this embodiment, each extraction module 302 is implemented in a manner discussed above. For example, each extraction module can be implemented in a manner discussed above in connection with the extraction system 100' depicted in FIG. 7. In this embodiment, each extraction module 302 includes its own dedicated fluid reservoir, though in other embodiments, a single fluid reservoir under the control of the controller can be shared among the extraction modules 302.

In this embodiment, the system 300 includes a multi-port manifold 306 that is coupled to the extraction modules 302. In this embodiment, the manifold 306 includes a port 306a through which wash media can be introduced into the fluid reservoirs of the extraction modules for washing the fluid reservoirs thereof. The manifold 306 also includes a waste port 306e through which the fluid contained in the fluid reservoirs can be drained into a waste container. The manifold 306 further includes a port 306b through which dry air can be circulated, e.g., from a compressed air source, to each of the extraction modules, e.g., to dry the fluid reservoirs, e.g., after the fluid contained therein is drained and the reservoirs are washed.

The system 300 can optionally include a UV spectrophotometer 308 that can receive samples of the fluid from each of the extraction units for spectral analysis thereof.

As noted above, the controller 304 can control the operation of the extraction modules. For example, in some embodiments, the controller 304 can operate two or more (or all) of the extraction modules 302 in parallel for concurrent controlled extraction and analysis of ingredients of a plurality of pharmaceutical dosage forms. The controller 304 can be implemented using known hardware and software in a manner known in the art informed by the present teachings.

Figure 15:
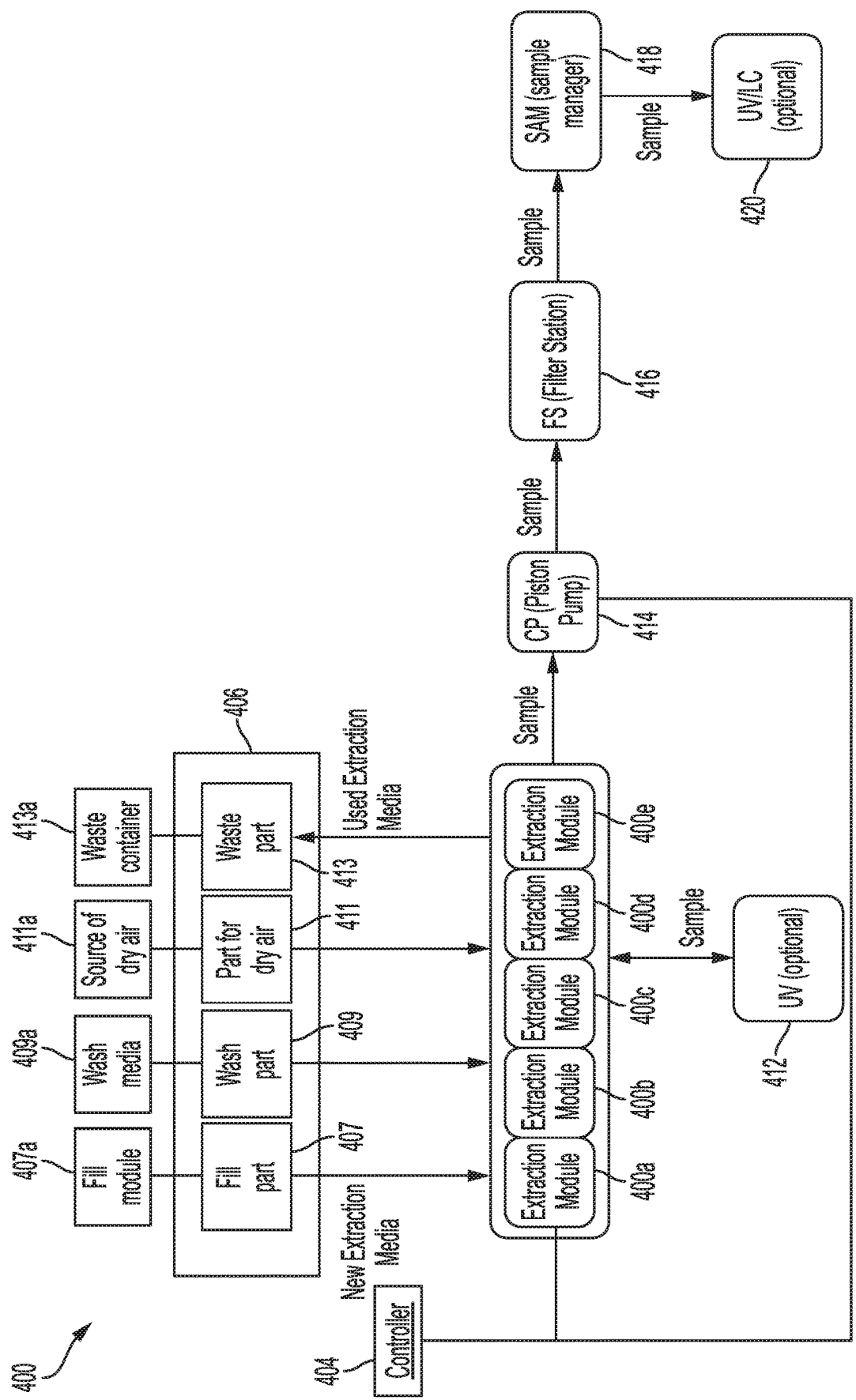

FIG. 15 schematically depicts another multi-unit system 400 in accordance with an embodiment, which includes, similar to the embodiment discussed above, a plurality of extraction modules 402a, 402b, 402c, 402d, and 402e (herein collectively referred to as extraction modules 402), which can be implemented in a manner discussed above, e.g., similar to the system 100' described above. A controller 404 controls the operation of the extraction modules 402. For example, similar to the previous embodiment, the controller 404 can operate the extraction modules 402 in parallel or individually.

The system 400 further includes a multi-port manifold 406 having a fill port 407, a wash port 409, a dry air port 411, and a waste port 413 for connecting the extraction modules to a fill medium 407a, a wash medium 409a, a source of dry air 411a and a waste container 413a, respectively. For example, the waste port can be used to drain the fluid from the fluid reservoirs of the extraction modules after the extraction of the ingredients of one or more pharmaceutical dosage forms is achieved. To prepare the extraction modules for subsequent use, the wash medium 407a can be introduced into the fluid reservoirs of the extraction modules via the wash port 409, and subsequently the fluid reservoirs can be dried via introducing dry air from the dry air source 411a, via the dry air port 411, into the fluid reservoirs. The fill port 407 can be used to fill the fluid reservoirs of one or more of the extraction modules with a solvent suitable for dissolving one or more pharmaceutical dosage forms disposed in those extraction modules. The extraction modules are then ready for reuse. In some implementations, one or more of the extraction modules can optionally include an inline UV spectrophotometer for inline spectral analysis of the ingredients of the pharmaceutical dosage forms dissolved in the circulating fluid.

In this embodiment, the fluid samples can be automatically extracted from the extraction modules via a pump 414, e.g., a piston pump, and can be transferred to a filter station 416 and a sample management module 418. Filtration will clarify the solution in order to have accurate reading by the spectrophotometer. The system can optionally include a UV/LC analysis module 420, which can receive one or more of the extracted samples for spectral and/or chemical analysis, e.g., in a manner discussed above.

Figure 16:
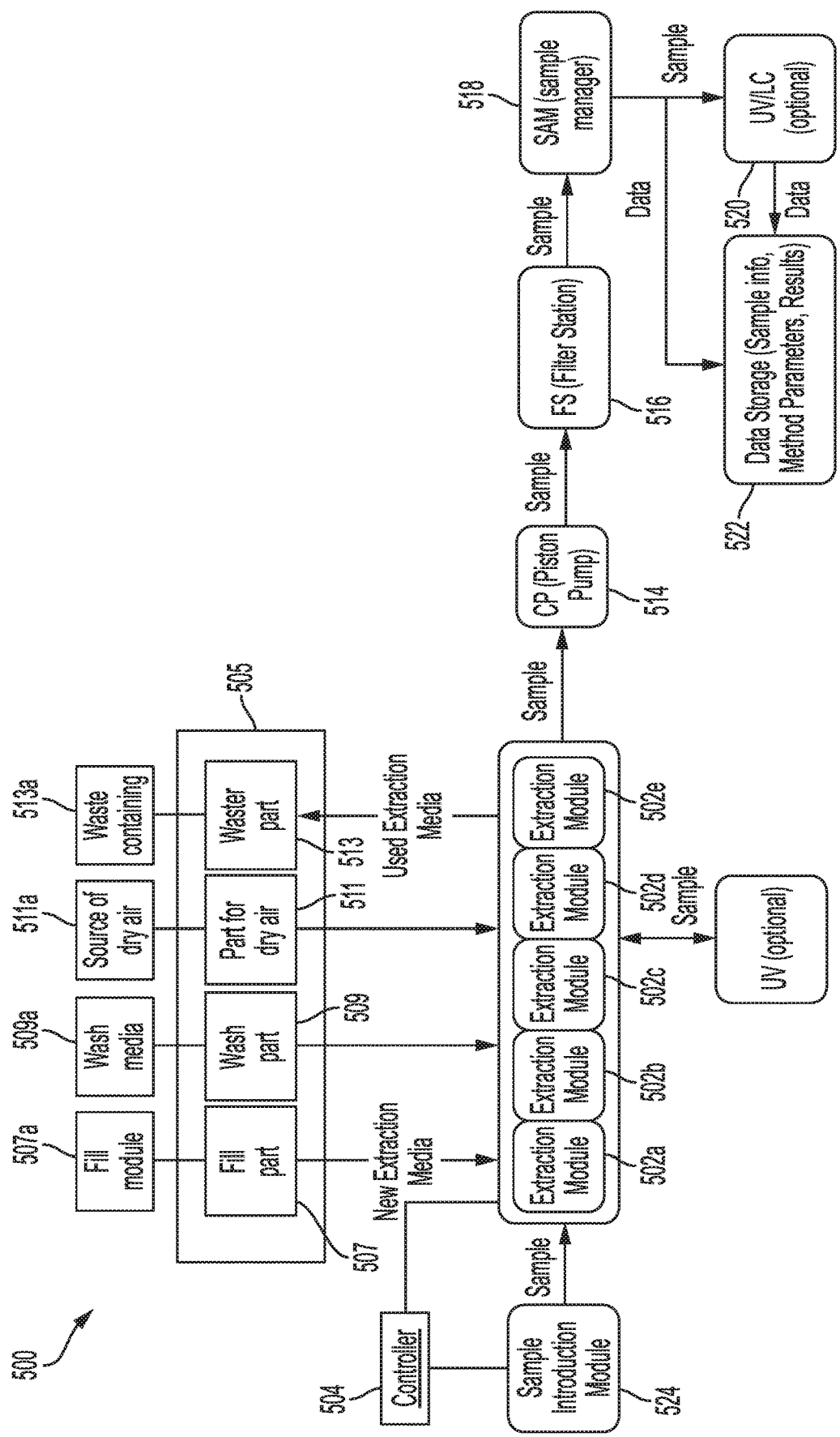

FIG. 16 schematically depicts another multi-unit embodiment 500 according to the present teachings that is fully automated to automatically receive one or more pharmaceutical dosage forms, subject the received pharmaceutical dosage forms to controlled extraction in a solvent, and automatically transfer the fluid containing the dissolved ingredients to an analysis module. Specifically, the multi-unit 500 includes a plurality of extraction modules 502a, 502b, 502c, 502d, and 502e (herein collectively referred to as extraction modules 502), which can be implemented in a way discussed above and operate under the control of a controller 504. Similar to the previous embodiment, the system 500 includes a multi-port manifold 505, which includes a fill port 507 connected to a fill medium 507a, a wash port 509 connected to a wash medium 509a, a dry air port 511 connected to a source of dry air 511a, and a waste port 513 connected to a waste container 513a.

The system 500 further includes a sample introduction module 524, which operates under the control of the controller 504, for automatically introducing one or more pharmaceutical dosage forms into one or more of the extraction units 502 to undergo controlled extraction of ingredients thereof. Similar to the previous embodiment, the fluid samples can be automatically extracted from the extraction modules via a pump 514, e.g., a piston pump, and can be transferred to a filter station 516 and a sample manager module 518. Filtration will clarify the solution in order to have accurate reading by the spectrophotometer. The sample management will collect samples in isolated vials so that they can be analyzed at a later timepoint. The system can optionally include a UV/LC analysis module 520, which can receive one or more of the extracted samples for spectral and/or chemical analysis, e.g., in a manner discussed above. The analysis data generated by the sample manager module 518 and/or the UV/LC analysis module 520 can be transmitted to a data storage module 522 and stored therein. This system advantageously allows fully automated controlled extraction and analysis of ingredients of one or more pharmaceutical dosage forms.

Figure 17:
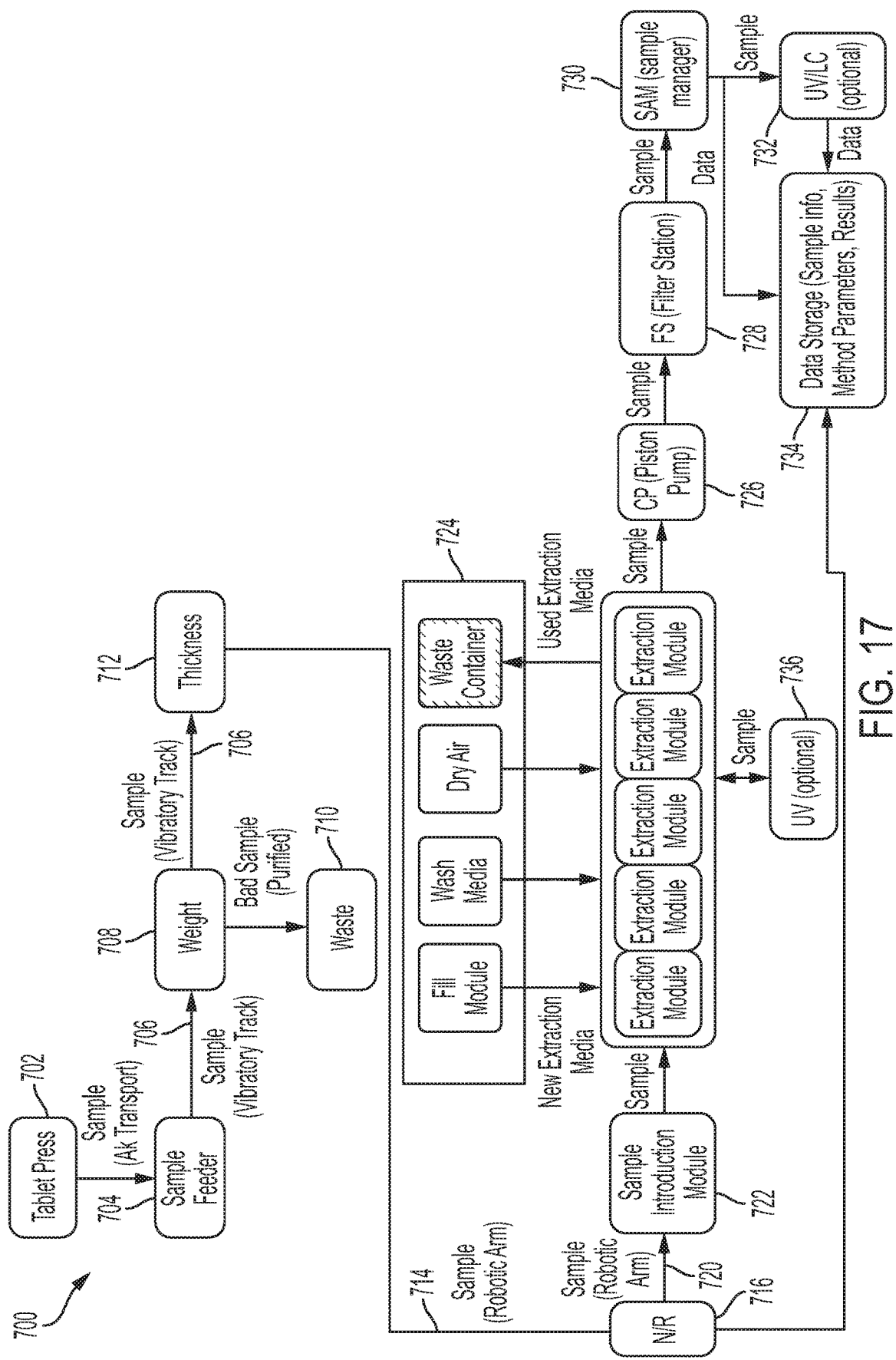

In another aspect, the present invention provides a fully automated system for performing quality control of pharmaceutical dosage forms. FIG. 17 schematically depicts an automated system 700 according to an embodiment for analysis of ingredients of a pharmaceutical dosage form. The automated system 700 is described herein by assuming that the pharmaceutical dosage form is a tablet. But the system 700 can be employed for analysis of other pharmaceutical dosage forms as well.

The system 700 includes a tablet press 702 that can receive a powder containing the ingredients of a tablet and press those ingredients into a tablet form. The tablet can be transported, e.g., via an air transport system, to a sample feeder 704. In this embodiment, a vibratory track 706 can be employed to transport the sample from the sample feeder 704 to a weight station 708, which is configured to measure the weight of the tablet. If the measured weight of the tablet is not within an acceptable range, the tablet is discarded by being pushed into a waste container 710. However, if the measured weight of the tablet lies within an acceptable range, the tablet can be transported, via the vibratory track 706, to a station 712 at which the thickness of the tablet is measured.

A robotic arm 714 can then be employed to transfer the tablet to a near infrared (NIR) and/or Ramen spectrometer 716 for spectral analysis of the tablet. The spectral data can show the content of the tablet and in some cases can be used to predict product performance. The spectral data generated by the NIR spectrometer can be transmitted to a data storage module 718 in which the analysis results including the measured parameters can be stored.

A robotic arm 720 transfers the tablet from the NIR spectrometer 720 to a sample introduction module 722, which can in turn transfer the tablet to a system 724 according to the present teachings for performing controlled temporal extraction of ingredients of the tablet. The system 724 is similar to the above systems 500 discussed above. The system 724 functions in a manner as that discussed above to extract the ingredient(s) of the tablet. In particular, as discussed above, the flow of the solvent stored in a fluid reservoir to a cell in which the tablet is disposed can cause the extraction of one or more ingredients of the tablet, e.g., via dissolution of the ingredients in the solvent. The fluid containing the ingredients can be collected in the fluid reservoir, in a manner discussed above.

A sample of the fluid contained in the fluid reservoir can be drawn from the fluid reservoir via a pump 726, e.g., a piston pump, and be transferred to a filter station 728. The filter station clarifies the sample solution in order to be evaluated spectroscopically. In some embodiments, multiple samples can be drawn from the fluid reservoir at a plurality of temporal intervals to collect data regarding extraction of the tablet ingredients at a plurality of times.

The filtered fluid can then be transferred, e.g., via a pump, to a sample manager module (SAM) 730, which is in communication with an analysis module 732 as well as a data storage module 734. The sample manager module 730 can transfer a portion of the fluid within the container to the analysis module 732, which can include a UV spectrophotometer as well as a liquid chromatography (LC) system for performing spectral and/or chemical analysis of the sample. The sample manager is also capable of dilutions if required prior to analysis. The analysis data can be transferred to data storage system for storage and further analysis.

The above system 700 can advantageously provide a fully automated system for quality control of a variety of pharmaceutical dosage forms, such as tablets. The system 700 can be incorporated into a work flow for fabricating pharmaceutical dosage forms.

Figure 18:
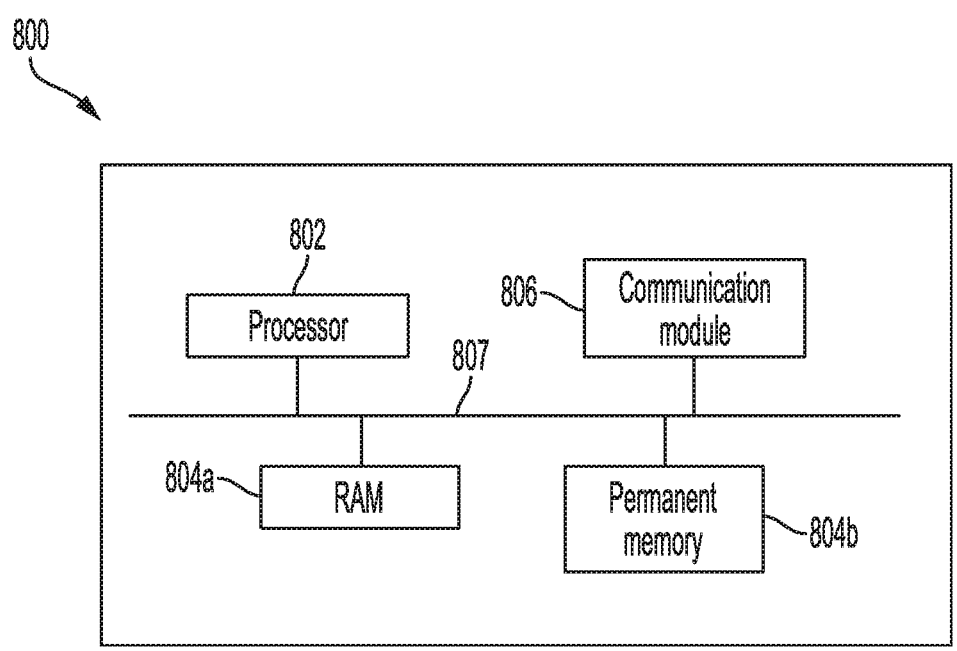

As discussed above, one or more controllers can be employed in various embodiments of systems according to the present teachings. Such controllers can be implemented using known hardware and/or software and employing methods known in the art. By way of illustration, FIG. 18 schematically depicts an example of a controller 800 that can include, among other elements, a processor 802, one or more memory modules 804, including a random access memory (RAM) 804a and a permanent memory 804b, communication module 806 for communicating with a controlled device, e.g., an extraction module, and a communication bus 807, which allows communication between the processor 802 and the other components of the controller. Instructions for controlling a device can be stored in the permanent memory 804b and can be transferred into the RAM 804a during run-time for execution. Data from the analysis can be sent electronically to data archival systems and/or to analytical systems where the analysis is occurring further streamlining the data workflow alongside the physical automation of the process.

Those having ordinary skill in the art will appreciate that various changes can be made to the above embodiments without departing from the scope of the invention.

What is claimed is:

1. A system for testing quality of a pharmaceutical dosage form, the system comprising:
   a weight station configured to receive the pharmaceutical dosage form and to measure a weight of the pharmaceutical dosage form;
   an extraction system configured to receive the pharmaceutical dosage form after the weight of the pharmaceutical dosage form is measured and to extract one or more ingredients of the pharmaceutical dosage form; and
   an analysis module configured to receive a sample of a fluid containing the one or more ingredients extracted from the pharmaceutical dosage form and to perform spectral or chemical analysis of the sample,
   wherein:
      the extraction system comprises:
         a cell having an inlet port and configured to receive through the inlet port the fluid containing the one or more ingredients of the pharmaceutical dosage form;
         a heater configured to heat the fluid before entering the cell through the inlet port;
         a first temperature sensor positioned between the heater and the inlet port, and configured to measure a first temperature of the fluid before entering the cell;
         a second temperature sensor positioned in proximity of an output port of the cell and configured to measure a second temperature of the fluid after the fluid exits the cell through the output port;
         a fluid reservoir configured to receive the fluid after the fluid exits the cell through the output port;
         a closed loop circulation path between the fluid reservoir and the cell;

a pump facilitating circulation of the fluid between the fluid reservoir and the cell; and a controller in communication with the heater, and further in communication with the first temperature sensor and the second temperature sensor, and configured to:

receive temperature data including the first temperature and the second temperature; and control the heater based on a measured fluid temperature derived from the first temperature and the second temperature; and the analysis module is configured to receive the sample of the fluid after the fluid exits the cell through the output port.

2. The system of claim 1, further comprising a vibratory track for transferring said pharmaceutical dosage form to the weight station.

3. The system of claim 1, further comprising a filter coupled to said pump for receiving said extracted one or more ingredients.

4. The system of claim 1, wherein the controller is further configured to control the heater based on a desired temperature.

5. The system of claim 4, wherein the controller is configured to control the heater based on comparing the measured fluid temperature with the desired temperature.

6. The system of claim 1, wherein the measured fluid temperature is an average fluid temperature derived from an average of the first temperature measurement and the second temperature measurement.

7. The system of claim 1, wherein the controller is configured to control the heater based on comparing the measured fluid temperature with a desired temperature.

8. The system of claim 6, wherein the controller is configured to control the heater based on comparing average fluid temperature with a desired temperature.

9. A system for testing quality of a pharmaceutical dosage form, the system comprising:

an extraction system configured to receive the pharmaceutical dosage form and to extract one or more ingredients of the pharmaceutical dosage form; and an analysis module configured to receive a sample of a fluid containing the one or more ingredients extracted from the pharmaceutical dosage form and to perform spectral or chemical analysis of the sample, wherein:

the extraction system comprises:

a cell having an inlet port and configured to receive through the inlet port the fluid containing the one or more ingredients of the pharmaceutical dosage form;

a heater configured to heat the fluid before entering the cell through the inlet port;

a first temperature sensor positioned between the heater and the inlet port, and configured to measure a first temperature of the fluid before entering the cell;

a second temperature sensor positioned in proximity of an output port of the cell and configured to measure a second temperature of the fluid after the fluid exits the cell through the output port;

a fluid reservoir configured to receive the fluid after the fluid exits the cell through the output port;

a closed loop circulation path between the fluid reservoir and the cell;

a pump facilitating circulation of the fluid between the fluid reservoir and the cell; and a controller in communication with the heater, and further in communication with the first temperature sensor and the second temperature sensor, and configured to:

receive temperature data including the first temperature and the second temperature; and control the heater based on a measured fluid temperature derived from the first temperature and the second temperature; and the analysis module is configured to receive the sample of the fluid after the fluid exits the cell through the output port.

10. The system of claim 9, wherein the controller is configured to control the heater based on a desired temperature.

11. The system of claim 10, wherein the controller is configured to control the heater based on comparing the measured fluid temperature with the desired temperature.

12. The system of claim 9, wherein the measured fluid temperature is an average temperature derived from an average of the first temperature measurement and the second temperature measurement.

13. The system of claim 9, wherein the controller is configured to control the heater based on comparing the measured fluid temperature with a desired temperature.

14. The system of claim 12, wherein the controller is configured to control the heater based on comparing the average fluid temperature with a desired temperature.

15. The system of claim 9, wherein the analysis module includes at least one of a liquid chromatography system and a spectrometry system.

* * * * *